US006454460B1

(12) United States Patent
Ramanathan et al.

(10) Patent No.: US 6,454,460 B1
(45) Date of Patent: Sep. 24, 2002

(54) SYSTEM AND METHOD FOR EVALUATING AND CALIBRATING A RADIATION GENERATOR

(76) Inventors: Naganathasastrigal Ramanathan, 37 Bankview Circle, Rexdale, Ontario (CA), M9W 6S6; Vijay Ramanathan, 37 Bankview Circle, Rexdale, Ontario (CA), M9W 6S6

( * ) Notice: Subject to any disclaimer, the term of this patent is extended or adjusted under 35 U.S.C. 154(b) by 0 days.

(21) Appl. No.: 09/149,517

(22) Filed: Sep. 8, 1998

(51) Int. Cl.[7] .............................................. G01D 18/00

(52) U.S. Cl. ....................................... 378/207; 378/158

(58) Field of Search .......................... 378/16, 108–112, 378/117, 118, 157–159, 207

(56) References Cited

U.S. PATENT DOCUMENTS

| | | | |
|---|---|---|---|
| 4,189,645 A | | 2/1980 | Chaney et al. |
| 4,355,230 A | | 10/1982 | Wilson et al. |
| 4,361,900 A | | 11/1982 | Siedband |
| 4,400,821 A | | 8/1983 | Aichinger et al. |
| 4,426,720 A | * | 1/1984 | Friedel ........................ 378/93 |
| 4,442,496 A | | 4/1984 | Simon et al. |
| 4,601,051 A | * | 7/1986 | Santurtun et al. ........... 378/118 |
| 4,697,280 A | | 9/1987 | Zarnstorff et al. |
| 4,843,619 A | | 6/1989 | Sheridan |
| 4,935,950 A | | 6/1990 | Ranallo et al. |
| 5,081,664 A | | 1/1992 | Lie et al. |
| 5,400,378 A | * | 3/1995 | Toth ............................ 378/16 |
| 5,530,735 A | * | 6/1996 | Gard et al. .................. 378/207 |

OTHER PUBLICATIONS

Ramanathan, N. and Paron, J. *Filters for chest radiology, Society of Photo–optical Instrument Engineers*, vol. 233 Application of Optical Instrumentation in Medicine VIII (1979), pp. 152–157.

Campbell, C.C.M., Yaffe, M. J., and Taylor, K. W. *Measurement of time variations of x–ray beam characteristics, Society of Photo–optical Instrument Engineers*, vol. 173 Application of Optical Instruments in Medicine VII (1979), pp. 312–317.

Sashin, D. et al. *Computer electronic radiography for early detection of vascular disease, Society of Photo–optical Instrument Engineers*, vol. 173 Application of Optical Instruments in Medicine VII (1979), pp. 88–97.

Tesic, M.M. et al. *Digital Radiography of the Chest: Design Features and Considerations for a Prototype Unit, Radiology*, vol 148, No. 1, (1983), pp. 259–263.

Sones, R.A., Morgan, D.R., and Tesic, M.M. *Measured performance characteristics of a solid–state linear detector array, Medical Physics*, vol. 12(2), 1985, pp. 135–142.

(List continued on next page.)

*Primary Examiner*—David P. Porta
(74) *Attorney, Agent, or Firm*—Dorsey & Whitney LLP

(57) ABSTRACT

A method and multipurpose apparatus that can evaluate an x-ray system performance for the purposes of quality assurance testing, servicing, optimization of technique factors and on-line x-ray source control. The apparatus offers self-consistent evaluation of kVp (Kilovolts Peak), Half Value Layers (HVL), x-ray exposure or kerma, exposure time, relative or calibrated mA, rise time, fall time, ripple factor and automatic identification of voltage or current spikes and break downs in a single x-ray exposure. This apparatus, by measuring radiation parameters from the same exposure, provides an accurate determination of parameters overcoming inconsistencies present in the traditional method of using several exposures. This apparatus uses a multiple sensor assembly with computer controlled electronics for optimization of signal conditioning and operational parameters. A filter package with varying material and thickness of x-ray attenuators in positions corresponding to sensors is used for self-consistent determination of kVp, mA, etc.

28 Claims, 16 Drawing Sheets

OTHER PUBLICATIONS

Tucker, D.M., Barnes, G.T., and Chakraborty, D.P. *Semiempirical model for generating tungsten target x–ray spectra*, Medical Physics, vol. 18(2), 1991, pp. 211–218.

Gambaccini, M., Marziani, M., and Rimondi, O. *A fast non–invasive beam check for mammography x–ray units*, Physics in Medicine and Biology, vol. 39, (1994), pp. 1423–1435.

Tesic, M.M. et al. *A Prototype Digital Chest Unit: Design Features and Considerations*, submitted to Radiology, pp. 1–29, no date.

PMX III User's Manual, RTI Electronics, Chapter 6, *Waveform Analyzer*: article 1.1.1., No date.

PMX III User;s Manual, RTI Electronics, Chapter 7, *Specifications: article 7.2 I Required set time*, p. 7–6, no date.

PMX III User's Manual, RTI Electronics, Chapter 4, *Multimeter: article 4.7 Filtration dependence for kVp measurements*, pp. 4–39 to 4–43, no date.

* cited by examiner

SYSTEM AND METHOD FOR EVALUATING AND CALIBRATING A RADIATION GENERATOR

TECHNICAL FIELD

The present invention generally relates to a system for evaluating and tuning a radiation generator. In particular, the present invention relates to an apparatus intended for (a) performance evaluation of an x-ray generator, (b) evaluation of associated imaging system signals for servicing, (c) optimization of radiographic parameters for image contrast, patient entrance exposure and x-ray tube loading, and (d) on line feed back of performance parameters to x-ray generator control for improving the radiation output characteristics. This device, which is capable of handling several radiation induced and non-radiation based signal inputs, combined with novel data sampling and processing methods, provides a self-consistent method of measurement for every single x-ray exposure.

BACKGROUND OF THE INVENTION

X-ray imaging is a popular clinical diagnostic imaging modality. X-rays cause damage to tissues due to their ionizing power. Image quality is fundamental to diagnosis while minimal x-ray exposure reduces patient radiation risk. In order to effect these twin goals, government bodies and professional organizations have enacted performance standards for x-ray imaging systems. Performance of x-ray systems is determined by measuring radiation. If a system is found to be non-compliant with the expected standards, corrective action is taken and servicing of the equipment is performed. Service personnel use test devices to measure electrical signals and identify problems for correction. An apparatus, which can provide both types of measurements, would help quick service and recalibration. Radiation based measurements, [ref. 12,9,7,6,5,4,3,1] currently used, include kVp (kilovolts peak), mA (milliamperes), HVL (half value layer), radiation exposure [ref. 8,2,1], exposure time, and radiation waveform [ref. 12].

X-ray energy spectrum is continuous, modeled by bremsstruhlung theory, with the highest energy of the spectrum [ref. 11] determined by the peak applied potential kVp. For the same kVp, different types of generators such as single phase, three phase six pulse, three phase twelve pulse, single phase medium frequency (variable), or high frequency inverters would produce different energy distributions. The mA determines the intensity or number of x-rays of an exposure without changing the energy distribution of x-rays. Since kVp can not describe the energy of radiation due to the spectral distribution, measurement of Half Value Layer (HVL) representing the effective energy with respect to attenuation by aluminum is necessary. This is usually obtained using data in several separate exposures of radiation output placing different thickness of aluminum filters in the path of radiation. This measurement procedure requires the x-ray generator is working under reproducible conditions. This assumption is questionable, particularly in the context of quality control testing. If we have determined the distribution of applied voltage and attenuation of radiation at each voltage for several thickness of filters, for the same radiation exposure simultaneously, then we can compute HVL consistently. In order to accomplish the above measurements, several novel design concepts have to be developed and implemented.

From a servicing point of view, rise time of x-ray exposure, pulse overshoot, and any high voltage breakdown due to x-ray tube problems require sample times in the range of 10–50 microseconds. Devices with analog electronics having a bandwidth of 1 kHz and 10 KHz analog-to-digital converter system can not detect these problems.

For self-consistent x-ray measurements, radiation parameters [ref. 10] such as kVp. HVL, mA, exposure time, exposure or kerma should be evaluated at the same time for an exposure. Corresponding waveforms should be processed for the same exposure as well. If this can be accomplished, this device would reduce number of exposures for evaluation, identify system performance with minimal uncertainty and self-consistency.

Non-invasive methods of estimating kVp from radiation measurements have proven to be useful. Currently popular method of kVp evaluation is based on radiation measurements using differential methods. The kVp measurement, ideally, should be performed for the whole exposure. Several designs have set a practical limit on the inclusion of exposure data for 100 milliseconds to 300 milliseconds. Actual exposures, as per generator specifications can be as long as 10 seconds. Exposure stability problems could appear in a long exposure, as x-ray tubes become gassy. Thus, exposure time limit for kVp measurement leaves critical problem areas unattended.

Among the inputs to the performance evaluation apparatus, two classes of signals are involved. Signals from x-ray assembly are fast, following the generator frequency. Signals from ionization chamber, mA meter, photo-timer output are integrated signals with less than 1 KHz bandwidth. Signals from circuits for exposure start, exposure terminate, rotor ready, filament ready etc. are, perhaps, pulses with several seconds of delay between their occurrence.

SUMMARY

Accordingly, the present invention offers the flexibility for measuring any combination of signals, thus advancing measurement procedures to technological limits.

This invention has accomplished to overcome the design limitations by devising a suitable component architecture and implementation. Measurement limitations have been removed by designing a multiple sensor inputs assembly and an automatic scan method to sample high frequency and low frequency signals from radiation sensors and electrical interfaces in the same exposure. Suitable computational procedures have been developed to arrive at accurate performance parameters and waveforms of the x-ray generator. Thus, this invention has succeeded in achieving self-consistent performance parameters of x-ray system. In addition to performance evaluation, this apparatus is useful for optimization of patient entrance skin exposure and image contrast. This apparatus can be extended to feed performance information back to generator control for on line adjustments for improved performance levels for accurate x-ray imaging applications.

In general, a system is provided that includes a multiple sensor assembly, a filter assembly, and a processor assembly. The multiple sensor assembly has a plurality of radiation sensors arranged to receive a radiation signal from a radiation generator. Each radiation sensor has a sensor output for providing a radiation sensor signal to the processor assembly. The filter assembly has a filter panel for at least one of the radiation sensors with each filter panel having an associated radiation sensor and being operably interposed between the radiation generator and its associated radiation sensor. The processor assembly is operably connected to the multiple sensor assembly to communicate with the multiple sensor assembly in order to receive the radiation sensor signals for evaluating the performance of the radiation generator.

In one embodiment, the invention includes (1) a multi-sensor assembly, (2) personal general purpose computer controlled electronics for signal conditioning and optimization, (3) a personal computer interface card that includes a programmable gain amplifier, multiplexer, analog-to-digital converter and digital input-output interface, (4) a personal computer with storage, (5) an application software or firmware for x-ray system performance evaluation and (6) personal computer compatible input and output devices. The multi-sensor assembly includes several x-ray sensitive sensors, which are substantially more efficient [ref. 18,14,13,1] for x-rays than simple silicon photodiodes. This is accomplished either by optically coupling silicon photodiodes with x-rays-to-light converting screens or materials used in radiography and fluoroscopy or using large area photo-conductive devices. The sensor devices are operated with bias and with device output optimized by load resistors. The computer controls the operating conditions and load on the sensors, through software and analog switches, depending on the signal and prior knowledge of x-ray system test conditions available from an integrated database. The system has the capability to determine optimal operating conditions of signal level, noise, and bandwidth for each exposure, set the correct conditions, and collect signal data under optimal conditions. Each sensor is independently optimized, amplified, and digitized without any specific electronic configuration determining the application of a particular sensor for the purpose of a parameter measurement such as kVp, kerma or exposure, time etc.

Each sensor signal is amplified with a fixed gain. At the time of digitization, the signal is amplified by a programmable gain amplifier (PGIA) and digitized to, say, 12-bit accuracy. The computer controls the gain of PGIA for the sensor signal, through software on the current and prior knowledge of x-ray system test conditions available from the integrated database. The system has the capability to determine optimal operating conditions for each x-ray exposure, set the correct conditions and digitize signal data under optimal signal conditions.

Sensor load, amplifier and PGIA cause an offset voltage signal. This offset requires cancellation before digitization so that actual radiation induced signal can be measured accurately without sacrificing the dynamic range of the analog-to-digital converter (ADC). Offset cancellation is accomplished by using differential inputs to PGIA with signal input and input from a digital-to-analog converter (DAC). When there is no radiation input, sensor signal is digitized and using this value the DAC is set with digital values to produce output voltage close to the offset. This process is continued iteratively to achieve a minimal offset of the system including ADC by software control from the computer. A FilterPak including radiation filter elements is placed in a fixed position assembly intercepting x-rays reaching sensors. The choice of materials and the thickness of the filter element is performed depending on (1) x-ray application such as general radiography, dental radiography, mammography etc., (2) type of x-ray tube such as tungsten anode, molybdenum anode etc., and (3) type and thickness of added filtration. The number of filter elements and sensors is decided based on the x-ray application and accuracy required for self-consistent determination of x-ray performance parameters.

Inputs from external electrical signals such as kV, mA, photo-timer, lightmeter, external radiation sensors etc., can be fed to PGIA and digitized in real time along with the radiation sensors of the multi-sensor assembly. Service engineers require many of these external signals for troubleshooting and servicing. Thus the present invention combines the functions of traditional x-ray quality assurance (QA) devices and oscilloscope and excels in performance by acquiring these waveforms in real-time. In one embodiment of the invention, an integrated database is used; it can contain stored information of the following: (1) Calibration system details and performance characteristics, (2) Calibration curve parameter fits, (3) Sensor and electronic signal control and optimization information, (4) Information related to data acquisition signal order, sampling interval between successive sensor signals, sampling period, and data acquisition duration, (5) External signal conditioning and control information, (6) Information related to performance parameter accuracy and permissible deviations pertaining to regulatory requirements, (7) Information of measured performance parameters and waveforms to produce performance trends of parameters, (8) Information on diagnostics of performance or trouble-shooting of tested x-ray system, (9) Information on solutions or tips to overcome the performance problems, (10) Information on optimizing the entrance air kerma or patient dose for the x-ray system under test based on the measured performance parameters and theoretical parameters simulating x-ray system characteristics, and (11) Information on the corrections of performance parameters due to variations of x-ray system characteristics between calibration system and x-ray system under test. This database information is used automatically for the operation of this apparatus.

This invention accomplishes several functions based on x-ray system tests: (1) Regulatory compliance and QA checks, (2) System performance diagnosis and guidance for solutions, (3) System optimization in terms of patient entrance skin exposure or air kerma, (4) Optimization of x-ray exposure techniques, and (5) Optimization of image contrast. This apparatus is also a novel tool for service engineers for interactive calibration and adjustments of x-ray systems, such as general radiography, mammography, fluoroscopy, angiography, cardiography, and single plane and biplane special procedure systems.

An integrated spreadsheet permits creation of standard and custom styles or formats for reports, which may include text, tables, and color graphs. Processed results are automatically presented as reports in spreadsheet style. User can choose the graphs of interest from a dropdown list and resize as required for the report. Reports are displayed on the screen and are available for hardcopy output through any PC-media.

The present invention has implemented a system of self-consistent measurement of x-ray system performance—automatically measuring kVp, HVL, kerma, exposure time, and all related waveform parameters such as rise time, ripple, fall time, spikes, break-downs etc., in a single x-ray exposure. This is a fundamental part of this invention. This method overcomes the uncertainties in determining performance parameters using several separate x-ray exposures. Multi-sensor arrangement in conjunction with suitable FilterPak helps acquiring self-consistent radiation data for evaluation of parameters automatically. Using appropriate FilterPak, the self-consistent evaluation method is applicable for any x-ray system used for general radiography, mammography, dental radiography, fluoroscopy, angiography, cardiography, and single plane and biplane, special procedure systems etc.

In addition to regulatory checks of performance standards of individual parameters, this apparatus analyzes systematically the performance parameters based on complete test. Behavior of x-ray tube output, HVL, relative mA, pulse frequencies in radiation waveforms, ripple, and rise and fall time values are considered with respect to, for example, with respect to kVp are considered for any substantial change to identify any corrective or preventive steps. This would have an appreciable impact in early diagnosis and suitable preventive maintenance avoiding surprise system failures and saving costs.

By choosing suitable material and thickness mimicking tissues for the FilterPak, image contrast performance of x-ray system can be studied for exposure without using film. This device permits image contrast evaluation using sensor signals quickly and accurately for range of operation of the system. Theoretical guidance using measured data is offered for optimizing contrast by selection of suitable kVp, and added filtration material and thickness. At the same time, patient entrance skin exposure or air kerma is also reduced by choice of appropriate added filtration material and thickness. This approach to optimization of contrast, technique (kVp) and patient exposure (dose) using FilterPak is applicable to any x-ray system used for general radiography, mammography, dental radiography, fluoroscopy, angiography, cardiography, and single plane and biplane, special procedure systems etc. This optimization capability is also a unique aspect of the invention. In combination with system performance evaluation capabilities, this apparatus provides a simple and practical method to improve the imaging performance of the x-ray system while minimizing patient dose.

The present invention is capable of self-consistent performance evaluation for radiographic x-ray exposures (radiation pulse) and fluoroscopic exposures (continuous radiation). For fluoroscopy, determination of kVp, exposure (dose) rate, HVL etc. are performed simultaneously. In addition, stability of these parameters over a period of several minutes can be determined as well. For x-ray systems, which use film camera (70 mm, 105 mm, cine camera etc.) or digital camera this apparatus measures self-consistent performance parameters for each exposure pulse of the complete exposure including several pulses. Stability, mean and deviations of self-consistent parameters of exposure pulses over the whole run are also evaluated. Waveform analysis is also performed for the whole exposure run with the same data.

For correct operation of an x-ray system, a specific real time sequence of several electrical signals from generator control and generator system component interfaces are required by design. Acquiring these electrical control and interface signals along with radiation signals would help quick inspection, calibration, and trouble-shooting of the x-ray system. The present invention offers a method of assessment of real time signal sequences of electrical and radiation signals, and evaluation of time intervals, delays and self-consistent radiation based parameters for every x-ray exposure sequence.

The present apparatus provides several types of softcopy and hardcopy reports based on measurements, and theoretical simulated parameters: (1) Single exposure report for each x-ray exposure, (2) Summary report of a complete test, (3) Trends of parameters over several past tests, (4) System Diagnostics report, and (5) System solutions report. Each report may include waveforms, as selected by user. Reports are customizable as well.

DETAILED DESCRIPTION

Figure 1:
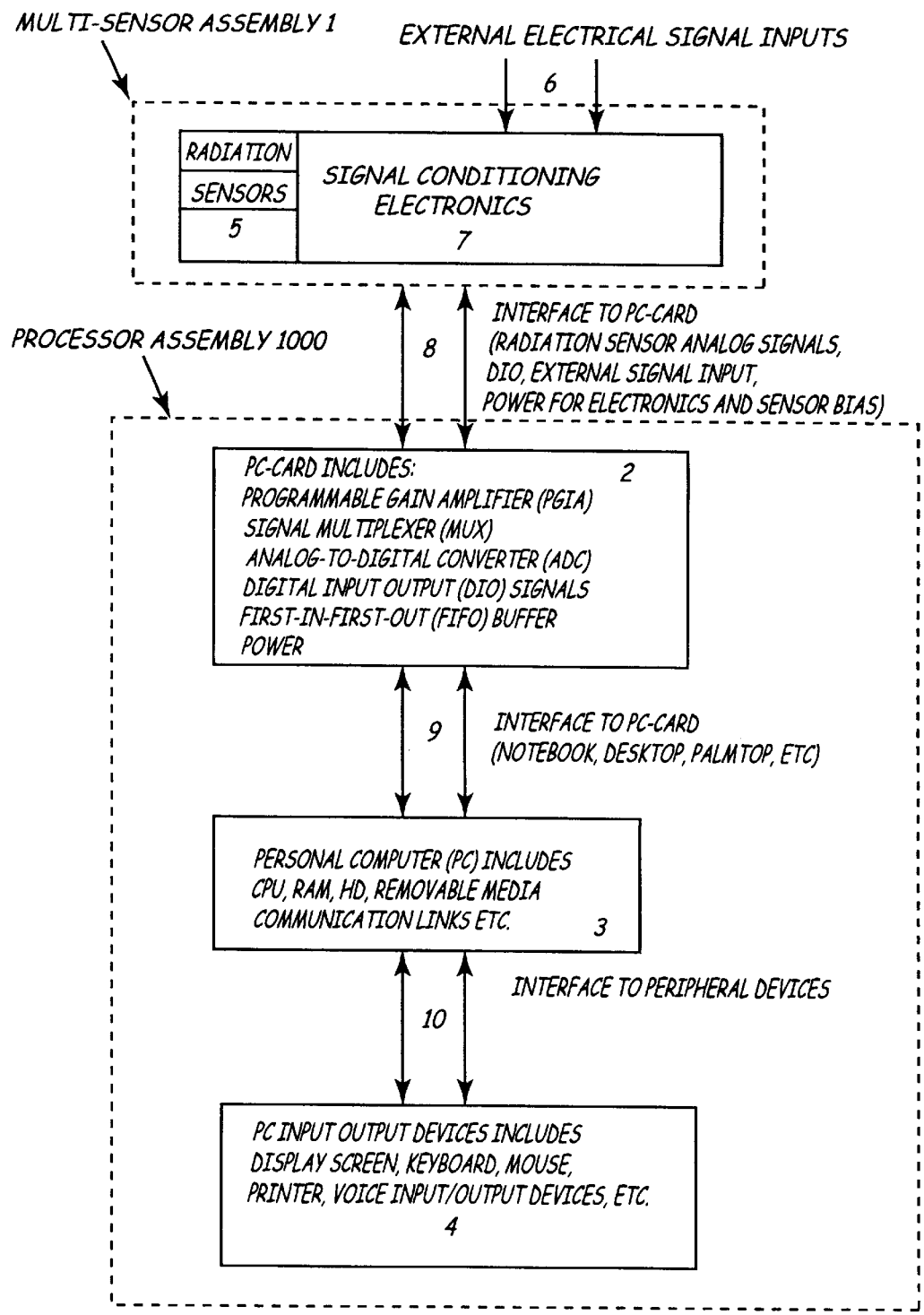
FIG. 1 shows a block diagram of one embodiment of an evaluation/calibration system of the present invention.
Figure 2:
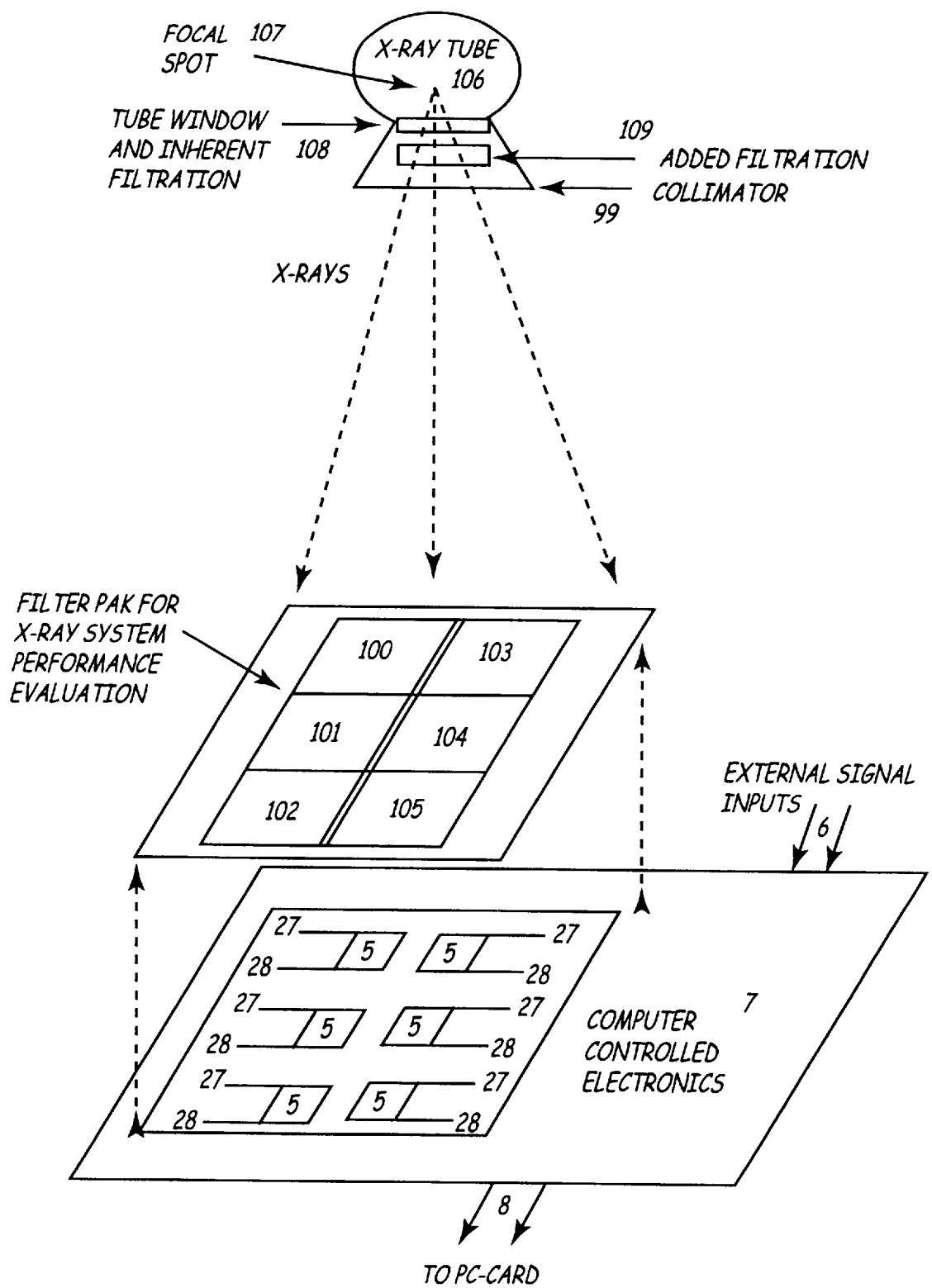
FIG. 2 shows a schematic view of one embodiment of a filter assembly and a multi-sensor assembly arrangement.
Figure 3:
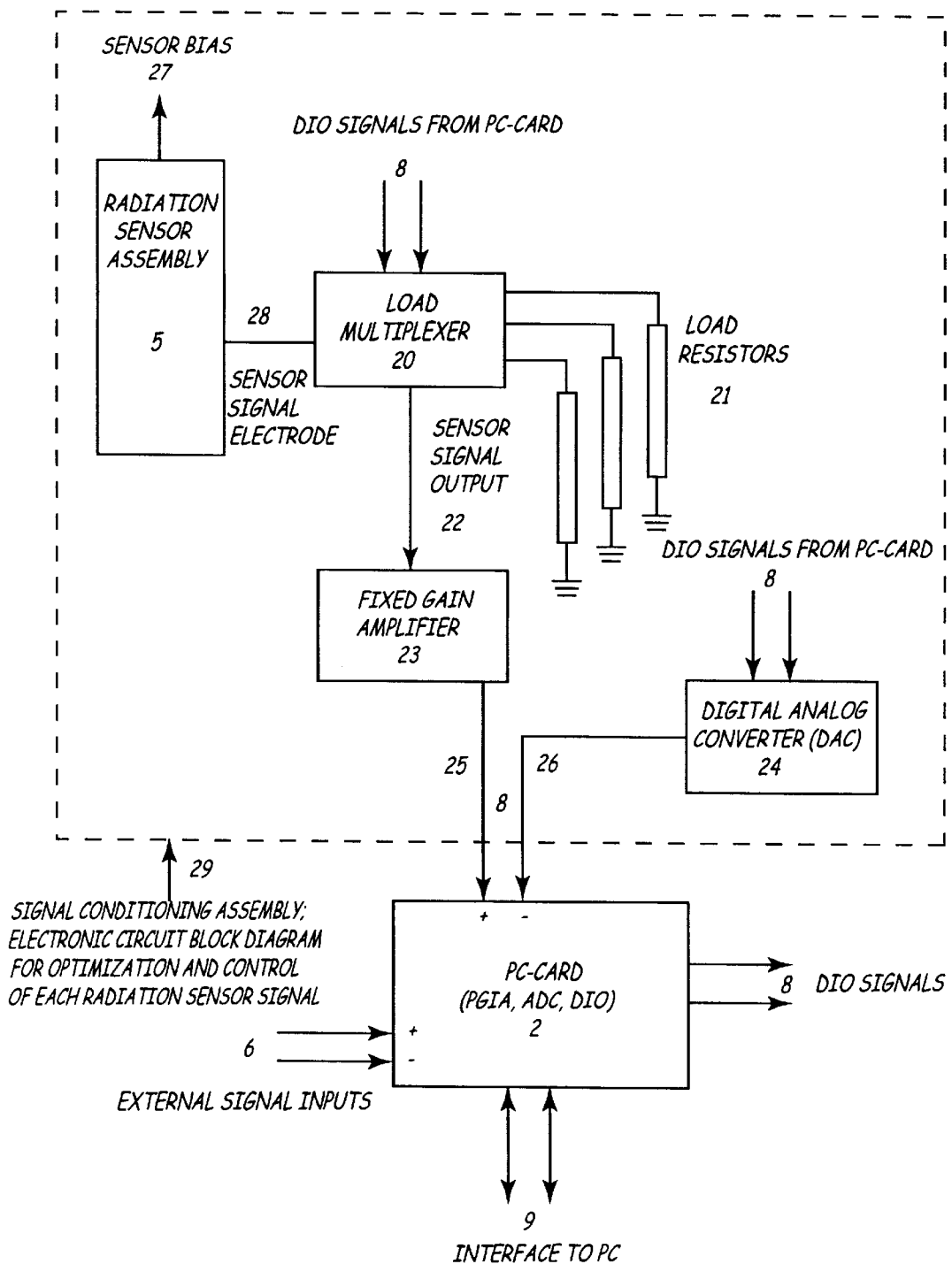
FIG. 3 shows a block diagram of one embodiment of a sensor assembly interfaced with a processor assembly.

With reference to FIGS. 1–3, one embodiment of an evaluation system is shown that includes a multi-sensor assembly 1 and a processor assembly 1000. Multi-sensor assembly 1 includes solid state radiation sensors 5, computer and PC-card controlled electronics 7, external electrical signal inputs 6, and interface 8 to PC-card including analog, digital input and output signals, power supply and control signals. Radiation sensors 5 include either a silicon photo-diode based assembly or photoconductive device. The sensors are enhanced such that x-ray absorption and energy transferred to produce signals or detector kerma is matched to x-ray imaging detectors such as screens in x-ray cassette. The property of reasonably matching x-ray response of sensor assembly to imaging detectors [ref. 18] extends use of this assembly for evaluation of image contrast. Several x-ray sensors are placed together in an arrangement so that the total area of placement is a minimum. When the sensors exposed to x-rays the beam intensity variation within the sensors' area is minimal. Typical placement is presented in FIG. 2. Multisensor configuration is an aspect of this invention.

Sensors are biased 27 and operated in photoconductive mode with a load resistor 21 determining the operating point and bandwidth. The specially designed circuit FIG. 3 incorporates analog switches controlled via Digital Input Output (DIO) signals of PC-card interface 8. Signal selection information is configured and stored in database 40, 41, 42, 43 for optimal performance. On line optimization of sensor performance FIG. 4 using PC-card interface, and database, by software or firmware is a fundamental part of this invention.

This solid state sensor assembly is used for self-consistent measurement of all radiation-based parameters kVp, kerma or exposure, kerma rate, HVL etc. Prior art [ref 1] uses different detectors for kerma and kVp and do not measure HVL for the same exposure. The sensors in the present invention are multi-purpose and not hardware configured, as in ref. 10, for any one specific parameter measurement such as kVp, or kerma or HVL by circuit design. The realization of on line optimized general-purpose sensor assembly for self-consistent evaluation of x-ray system performance a key aspect of this invention.

Specially designed sensor assembly electronics FIG. 3 include a fixed gain high bandwidth amplifier 23, DAC 24 and load resistor 21 for each sensor, and power supply. The output of amplifier and DAC is fed as differential inputs to PGIA of the PC-card 2. PC-card interface 8 handles amplified sensor signals 25, DAC signals 26. External Signal Inputs 6 and other DIO control signals. Use of an interface for high bandwidth sensor signals, DAC signals, control signals and power signal is an important part of this invention.

Figure 4:
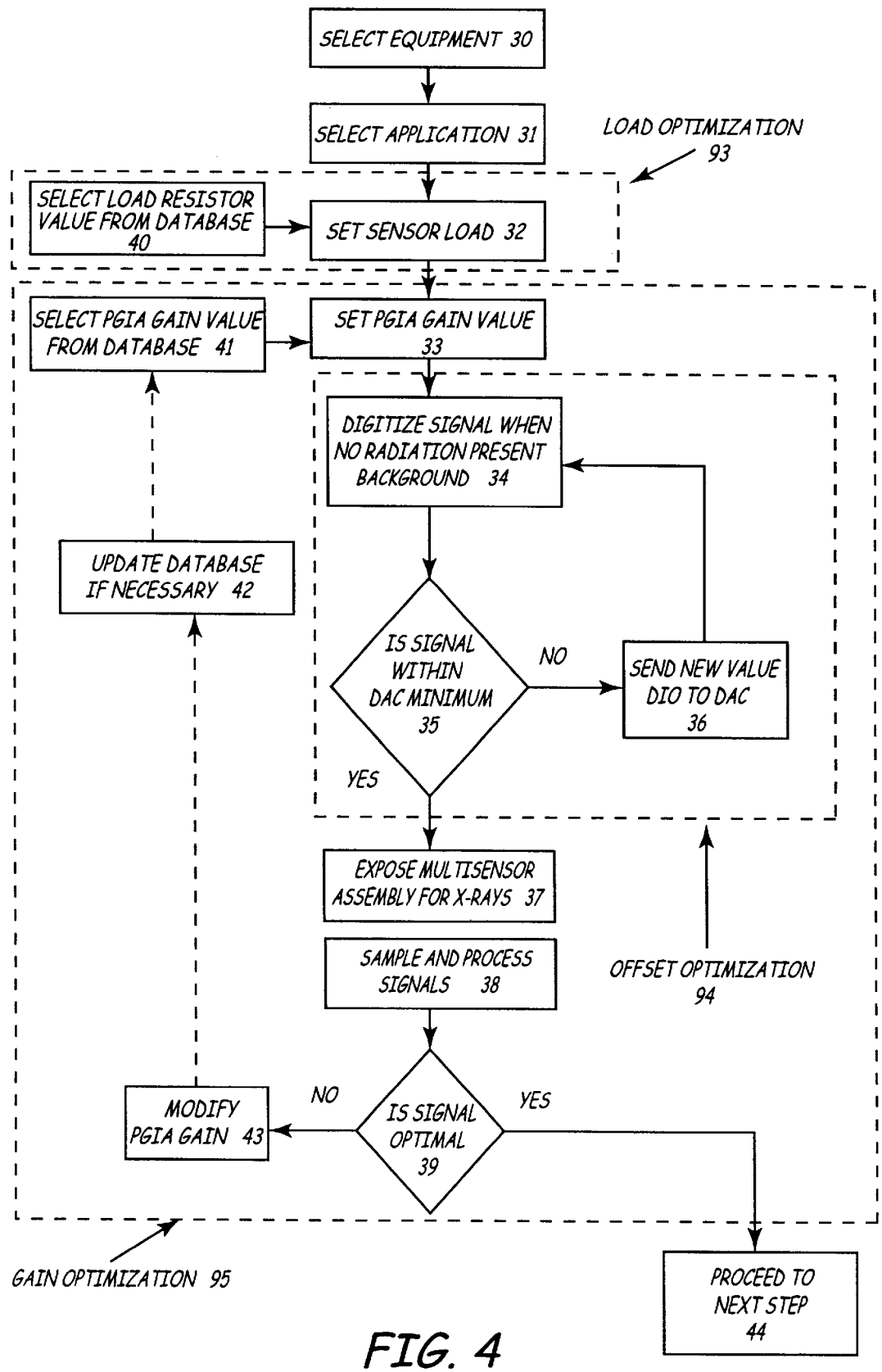
FIG. 4 shows a flow chart depicting a routine for optimizing a signal.
Figure 5:
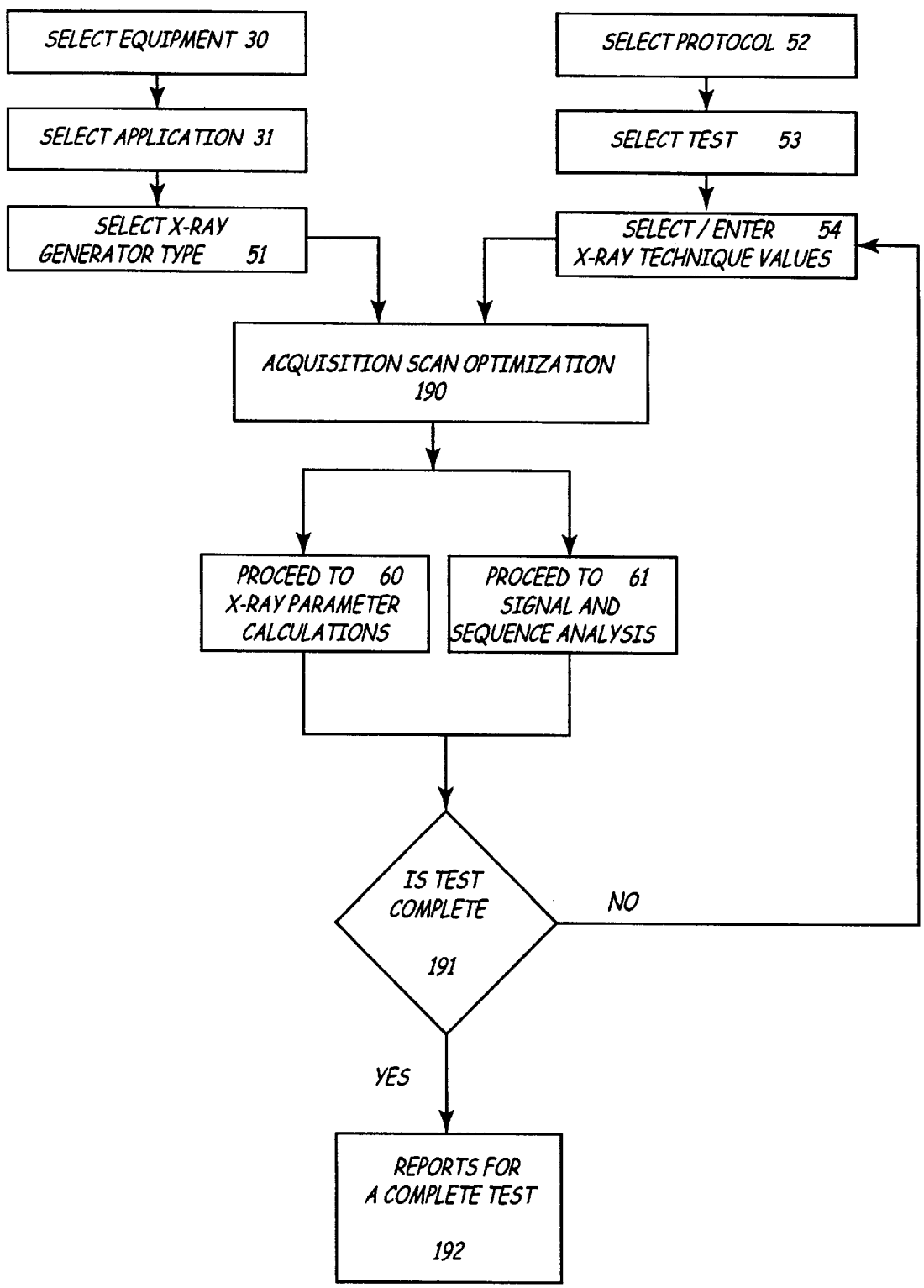
FIG. 5 shows a flow chart of a routine for performing a test on a radiation generator.

Offset Optimization procedure 94 as in FIG. 4 is accomplished by digitizing amplified radiation signals 25 when there is no radiation exposure. The digitized value is scaled suitably and corresponding DIO signals 36 are sent to DAC via interface 8. This novel approach provides offset cancellation for the analog sensor signal for that gain including any offset voltage due to ADC, PGIA, fixed gain amplifier, and sensor dark current at operating load conditions. DAC adjustment is accomplished using DIO signals until offset for that sensor signal or channel is a minimum.

Gain of PGIA is optimized 95 as in FIG. 4 for each x-ray exposure. This approach to offset and gain optimization of every sensor signal using Database 40,41,42,43 of optimal Load Resistor values, PGIA Gain values, and a means of iteratively updating and of evaluating optimal values 39 the for each exposure permits full dynamic range of ADC, minimal background signal and noise amplitude, and minimizes any effect of temperature. This is a basic part of this invention. The logic of signal optimization is sketched in FIG. 4.

Figure 9:
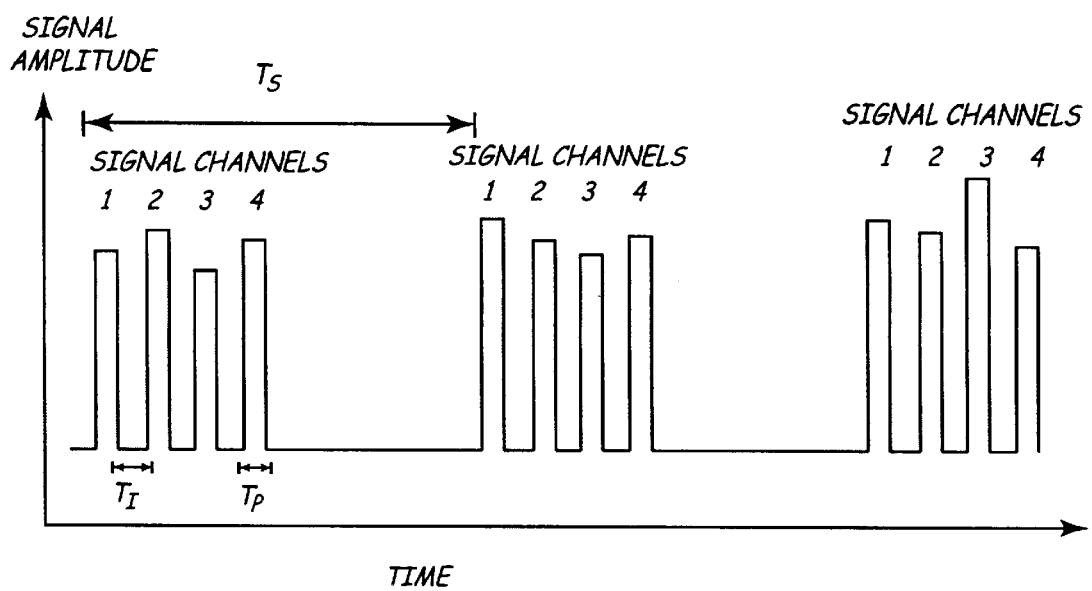
FIG. 9 is a sampling diagram of a sensor signal.

Signals from radiation sensors in assembly 25 and corresponding DACs 26 and external electrical signals 6 are suitably amplified digitized and data transferred to PC via interface 10. The digitization or sampling and data transfer process for an acquisition is called Acquisition Scan. Prior art [ref. 7,2] in this field had used digitization of signals continuously in a fixed frequency. In many cases, the sampling frequency was fixed for the whole operation of the apparatus irrespective of what type of generator the apparatus is measuring. Many of these apparatus had sampling frequency in the range of 10 kHz. The present invention uses an adaptable sampling method shown in FIG. 9, with sampling frequency depending upon the generator type 51, and number of signals (1,2,3,4 etc. in FIG. 9) to be sampled.

Real time sequential adaptable sampling method include three intrinsic time setting for sampling of all signals:

$T_P$, sampling period for a single signal;

$T_I$, time interval between sampling of two successive signals;

$T_S$, time interval between sampling of the same signal, called Scan Period.

A single Acquisition Scan include several scan periods. Database incorporates tables 56 of optimal scan and sampling parameters in terms of intrinsic time settings for each test and application. The settings determine amount of overall data collected and number of points required achieving maximum accuracy. It is important to set the scan period to be a fraction of the x-ray generator period $T_G$. In general, the following relationship will be set:

$N(T_P+T_I) \ll T_S \ll T_G$, where N is the number of signals processed.

Figure 6:
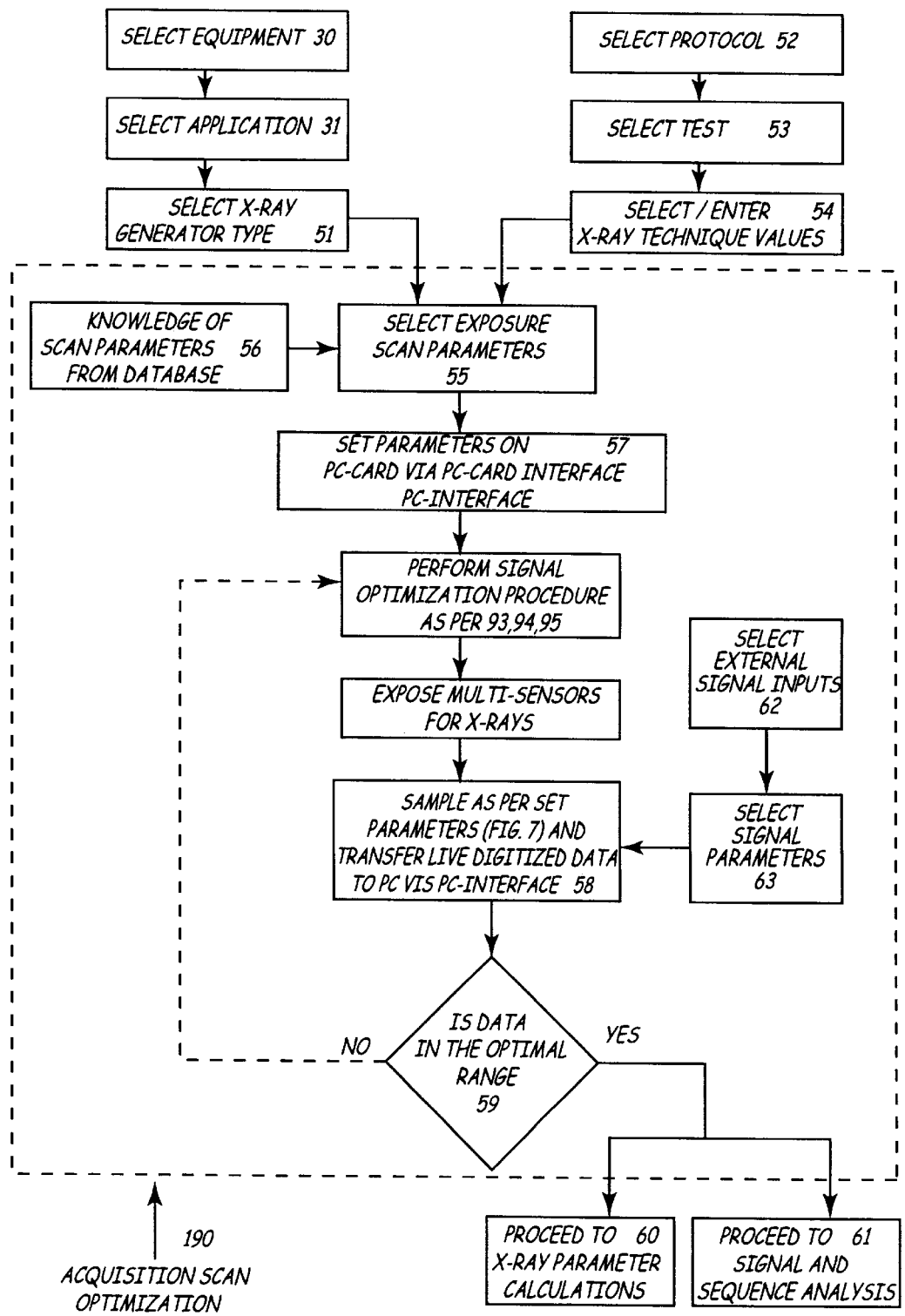
FIG. 6 is a flow chart depicting a scan parameters optimization procedure for x-ray exposure.

When all signals are sampled simultaneously, then $T_I=0$; this requires multiple ADCs and corresponding analog and digital circuit overhead. The present invention uses a generalized approach where the above relationship can be enforced as the specific measurement demands based on the test, parameter, generator, and technique parameters. Procedure for scan optimization for acquisition 190 is presented in FIG. 6. Scan optimization is performed for each exposure. It is important to note the types of scan optimization for single pulse exposure, and continuous exposure as in fluoroscopy exposure including several radiation pulses with non-radiation intervals as in angiographic imaging. Scan parameters are selected 55 based on selection of protocol 52, test 53, techniques 54 equipment 30, application 31 such as radiography, fluoroscopy, angiography etc., generator type 51, using knowledge stored in Database 56. The parameters are sent to PC-card 2 from PC via PC-interface 9. The digitized data is sent 58 to PC from PC-card via fast PC-interface 9 during the exposure. It is important that the interface can handle the required for loss-less data transfer. The capability to acquire, transfer, store and process complete exposure samples irrespective of length of exposure for radiation based signals and external signals as well at the same time is another important aspect of this invention.

The prior art [ref. 7, 16] used the first few (as high as 50) milliseconds of the x-ray exposure to adjust the signal optimization parameters and not use this part of the exposure for any other evaluation. An important problem with this approach is that if the radiation output is not proper during the first part, the rest of the exposure measurement is turned useless due improper signal optimization requiring repeated exposures without any results for prior exposures. The present invention clearly overcomes the problem. It is noteworthy that if a generator has performance problems, it would show up at the start of exposure. That is why an optimization, based on Database of knowledge and prior performance parameters, is a significant aspect of this invention.

Each test 54 involves determination of several performance parameters depending on the test. Each exposure requires evaluation in some tests. Thus there are single exposure report, test report and other types of report. Besides radiographic parameter evaluation 60, the analysis of raw signals 61 themselves provide insights of the performance, problems and service of the system. In the prior art [ref. 15] some of the radiographic parameters are evaluated in one exposure and some of the signal analysis is performed on another exposure. The present invention accomplishes both parameter and signal evaluations for each exposure, so those problems can be identified in a self-consistent manner. The evaluation is called self-consistent because all the simultaneous performance parameters associated with x-ray system are processed in one exposure while according to traditional methods those are evaluated using data from several exposures thereby introducing uncertainties just due to measurement method itself. The self-consistent measurement method determines true value of performance parameters. This is a fundamental difference in philosophy and implementation of this invention.

Figure 7:
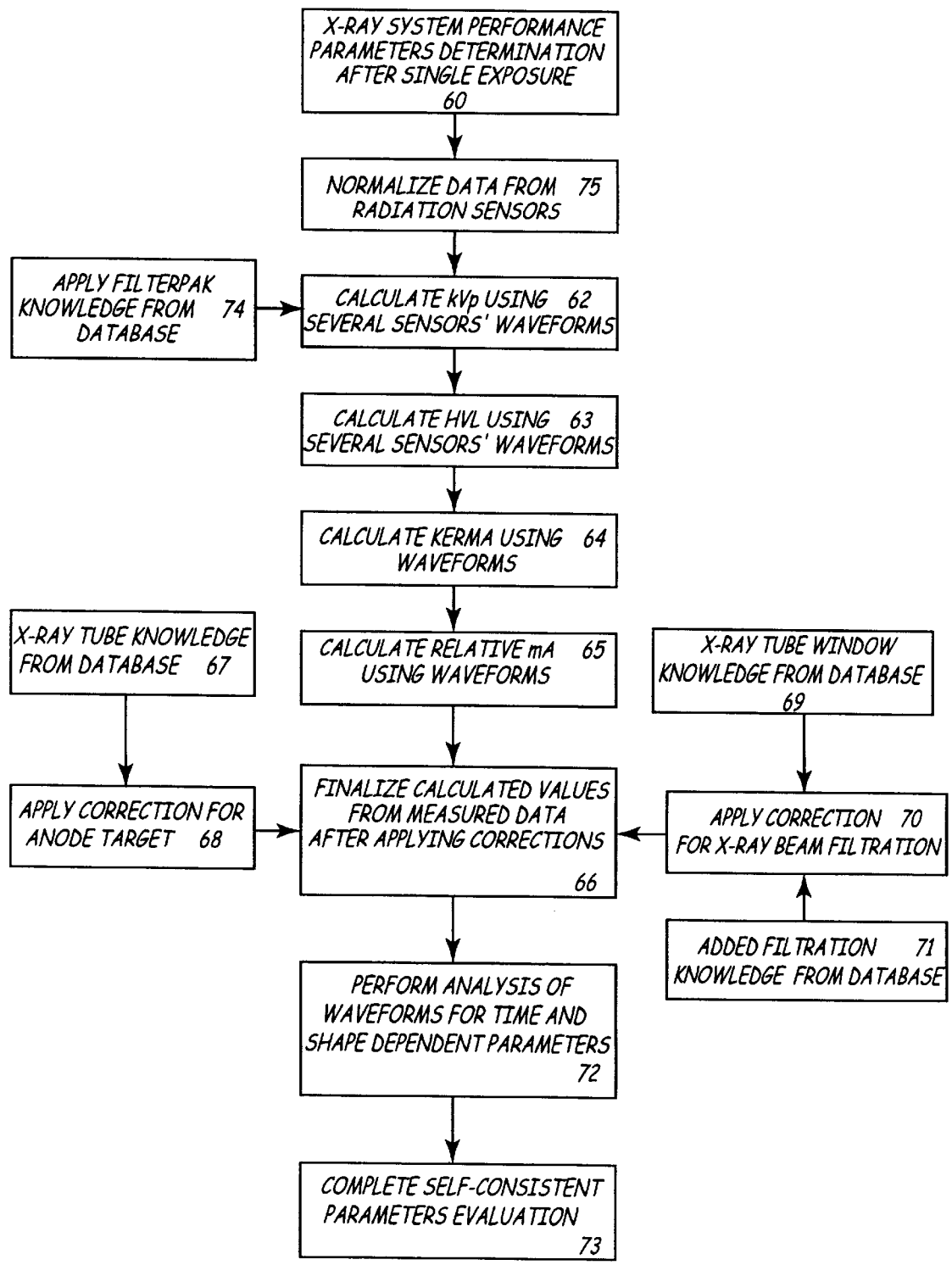
FIG. 7 is a flow chart depicting a self-consistent evaluation procedure using a single x-ray exposure.
Figure 8:
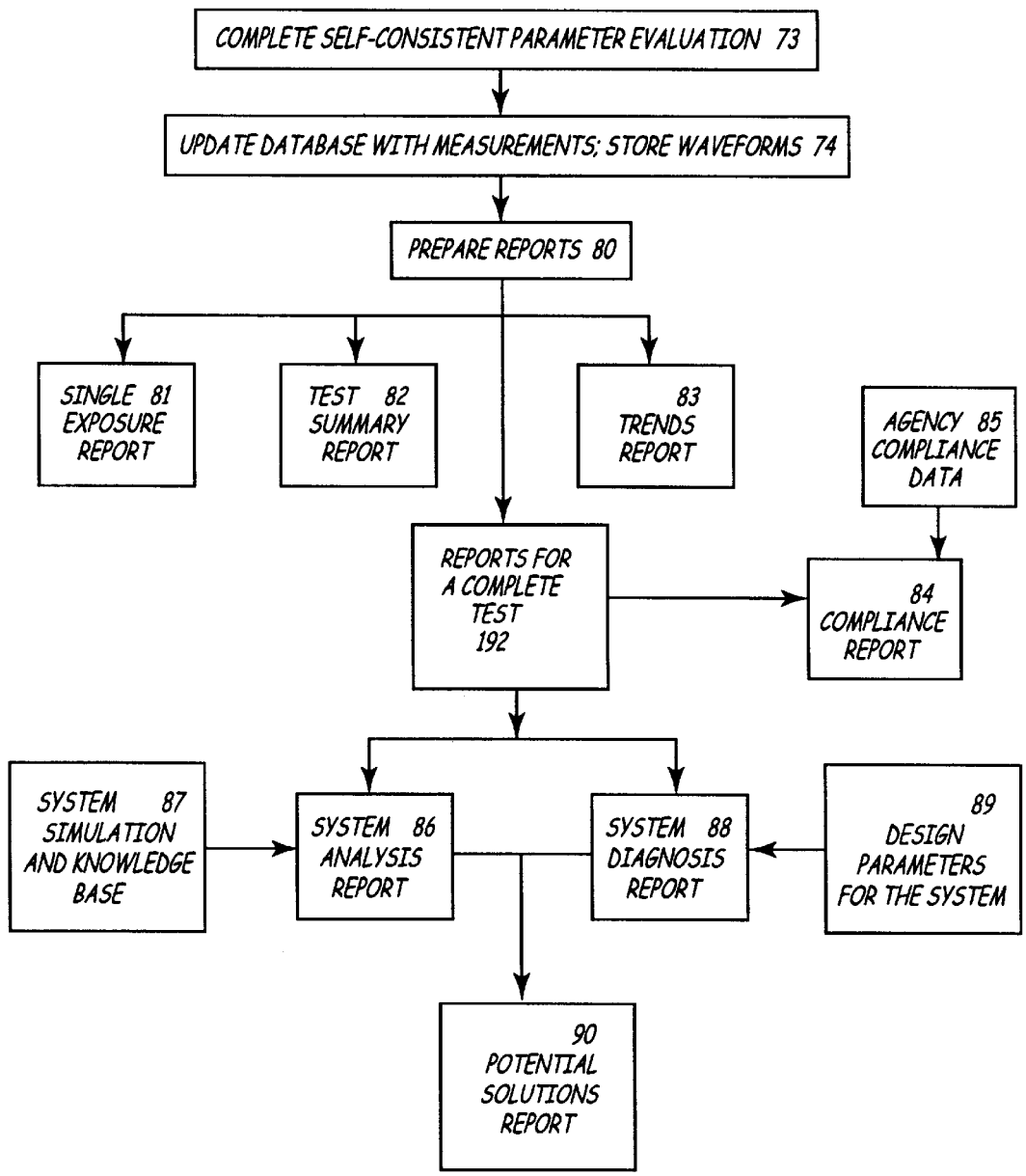
FIG. 8 is a flow chart of a reports generating procedure.

Procedure for determination of self-consistent performance parameters is presented in FIG. 7. Knowledge of the following items stored in database as entered by user first time they use a system for test:

FilterPak materials and thickness 74,
x-ray tube parameters 67 such as anode materials and anode target angle,
x-ray tube window 69 material composites made of glass or beryllium and inherent filtration, and
added filtration 71 material and thickness.

Correction of measured parameters 70 for inherent filtration 108 and added filtration 109, together with corrections 68 due to anode target material and angle provides a complete set of calibration corrections.

Since several sensors are used for acquisition, their data is first normalized 75 to account for variations in their sensitivity for radiation. Using the FilterPak information from database, 74 x-ray system performance parameters are determined. All sensors are sampled the same manner without dedicating any for a particular parameter. It is the FilterPak 110 material and thickness 100, 101, 102, 103, 104, 105 in a particular position that determines the attenuation of x-rays that reach the sensor. Depending on the application such as radiography or mammography, FilterPak material and thickness in each position is different. Thus FilterPak is designed for optimal attenuation and range of HVL for the specific application. One FilterPak 110 covers the range of a complete application.

FilterPak placed in position over the radiation sensors such that material in FilterPak at position 100, 101, 102, 103, 104, 105 intercepts x-rays reaching only one sensor completely. For example, no material may be present at position 100; material at positions 103, 104 and 105 could be aluminum of different thickness sufficient to evaluate HVL for the application; material at positions 101 and 104 can be made of a material with considerably higher atomic number differing in thickness. Sensors 500, 501, 502, 503, 504, and 505 corresponding to FilterPak materials 100, 101, 102, 103, 104, and 105 produce signals for evaluation of parameters using method of differential attenuation or ratios of signals and knowledge from database 74.

An important difference between prior art [ref 9,7,2,6, 1, 4,5,3] and the current invention is that a parameter can be calculated using several different ratios using data from different pairs of sensors and most accurate of the values is selected for the parameter. For example, for kVp determination 62, ratios of 501 and 500, 502 and 500, 502 and 505, 501 and 504, 504 and 501 would be evaluated. Depending on the ratio value and quality of data optimal one would be used as kVp before any correction is applied. In this method, if the set kVp and measured value were quite different, still measured value would be produced without requiring any other filter set up. The present apparatus is ready to measure an optimal parameter value for complete range of kVp within the application for every exposure irrespective of operator setting on kVp. Thus the design of FilterPak and Multi-sensor Assembly helps to evaluate complete range of an application at every exposure for self-consistent parameters kVp, HVL, kerma or exposure, time and other derived parameters without changing filter set up internally or externally. This is an important design aspect of the present invention.

A new approach to HVL measurement 63 has been achieved in this apparatus. At least, four sensor data can be used to evaluate HVL from a fitted function automatically for each exposure. The following is a brief description of the method:

Let signals 500, 503,504, 505 correspond to aluminum filter thickness $t_0$, $t_1$, $t_2$, $t_3$ in mm.

Let ratio $r_1$, $r_2$, $r_3$ correspond to ratio from data of signals 503/500, 504/500, 505/500.

Consider a polynomial function, $t(r)=\alpha_0+\alpha_1 f(r)+\alpha_2(r)$ where t represents thickness corresponding to ratio r and f(r) is a suitable function using ratio r as an independent variable. Note that for $t(r_0=1)=0$, for filter 100 corresponding to signal from 500. Using value $t_1$, $t_2$, $t_3$ from FilterPak database 74 and ratios $r_1$, $r_2$, $r_3$ from measured data the polynomial function can be fitted by any typical method. The values of thickness t in FilterPak 103, 104, 105 may cover the range of HVL for the range of kVp applicable. Multi-sensor assembly and FilterPak design do not limit the number of sensors or thickness. It is easy to implement a number of sensors and FilterPak thicknesses as needed. An example polynomial function, t(r) is given above but any suitable function or any degree function can be used for fitting depending on the data available. From the fit, the coefficients $\alpha_0$, $\alpha_1$, $\alpha_2$ etc., are determined. Then setting r=0.5, HVL is calculated from $t(r_{HVL}=0.5)$. By setting r=0.1 tenth value layer or any required thickness can be calculated depending on the thicknesses used and data quality. Basically the method adopted is flexible, accurate, requires a single exposure, self-consistent and unique aspect of the invention. Traditionally HVL is evaluated based on radiation exposure or kerma for the whole exposure. In the present apparatus this achieved by integrating data for the whole exposure from individual samples. It also possible to produce HVL waveforms by applying the same method to samples matched in time. HVL waveforms can indicate problems due to kV-waveform shape variations. The traditional HVL value may not be as sensitive to kV-shape variations as much as the HVL-waveforms. Ability to produce HVL waveforms is another unique aspect of this invention.

Determination of kerma in the present apparatus is performed from the solid-state sensors without using ionization chambers. Since all standards of kerma measurement require kerma using ion chambers or $kerma_{Air}$ we have to relate the measured sensor kerma or $kerma_{sens}$.

Writing the relationship as, $kerma_{Air}=kerma_{sens}$(kV (time), HVL) Note that kV is a function of time or instantaneous sample and kerma is a function of both kV and HVL. This functional relationship is obtained by calibration, then $kerma_{Air}$ is calculated using measured kV waveform and HVL. Thus corrections for variation in energy and beam quality are achieved in one step since both these values are readily available for each exposure. This is another unique aspect of this invention determining $kerma_{Air}$ corrected for energy and beam quality using a solid-state detector.

In the prior art [ref. 4], the design used radiation sensor data without any filtration to determine relative mA. The relative mA values obtained 65 in this approach would be sensitive to x-ray energy distribution and filtration at any kVp. If the data from heavily filtered beam is used for this purpose, the effect of energy distribution and filtration on mA value would be a minimum. If calibration of the sensors 501 and 502 with corresponding heavy filtration 101 and 102 were performed for mA in the kV range of the application, this would work as mA value for most cases. Even for system where mA varies, normalization of the measured relative mA value with a directly measured mA for one mA-position, will yield calibration for that system. Note that mA is defined as the average current. Since we have the waveform, we evaluate shape, frequency and average value of mA waveform. Thus, it is possible to obtain mA value using the present apparatus with a simple normalization. This is another aspect of the present invention.

The present invention implements a novel approach to application of corrections compared to the prior art [ref. 17]. For example, consider a calibration x-ray system with an added filtration of 3 mm aluminum. The system evaluated at the site may have an added filtration of 4 mm aluminum. According to prior art, correction for added filtration is done using experimentally measured and stored value of correction for some specifically selected cases. If the site test system does not match the any stored conditions of added filtration, operator is requested to remove and adjust the added filtration to match the calibration conditions for the purposes of specific tests. From this it is evident that the calibration parameters depend on the components of the x-ray system used for calibration. Another key factor that is not corrected in the prior art is the dependence of performance parameters on the anode composition and anode target angle. It is known that the anode target material composition and anode target angle influence the x-ray energy spectral fluence. Since we depend on the differential attenuation ratio for kVp determination, the kVp calibration would depend on the x-ray energy spectral fluence. Then this calibration factors if applied on a x-ray system with a different anode target material composition or anode target angle would introduce an error that depends on the variations between calibration x-ray tube and site x-ray tube.

For the calibration system let a component value be M yielding a parameter of C after a measurement. At a site, the corresponding component has a value M'. The parameter measured at the site using the previous calibration yields a value C'. Some components such as added filtration can be tested on calibration system can be tested and correction factor can be obtained for equivalent conditions. But parameter such as anode target angle can not be accounted for like that. Hence a fresh approach is required using either theory or measured data. It is possible to simulate a x-ray energy spectral fluence from theory or from available tabulated data of the same for some cases. With this method, let the simulated parameter corresponding to C be S and corresponding to C' be S'.

Let the calibration function be F(M,C).
Site parameter C'=F(M,C) D(M') where D is measured data at site with component M'.
Corrected site parameter C"=F(S', S) C'=F(S', S) F(M,C) D(M').

The transformation function F(S', S) corrects the calibration function F(M,C) for the component variation M'. This method is general and applicable to any performance parameter evaluation. It is important to note that F(S', S) involves relative change in the parameter and it is not necessary that absolute values of S' and S are required. Performance parameter values are finalized 66 after corrections are applied 68, 70 using database knowledge 67, 69 and 71 to account for changes due to components of calibration x-ray system and evaluation at site. This correction method is a unique aspect of this invention.

In addition to the above parameter computations, same acquisition data is used for waveform analysis. Waveform is automatically processed 72 for shapes of rise and termination, pulse peaks, valleys, breakdowns, overshoots, exposure time etc. Thus complete evaluation 73 of performance parameters and waveform analysis is achieved in a single exposure in a self-consistent manner.

Figure 10:
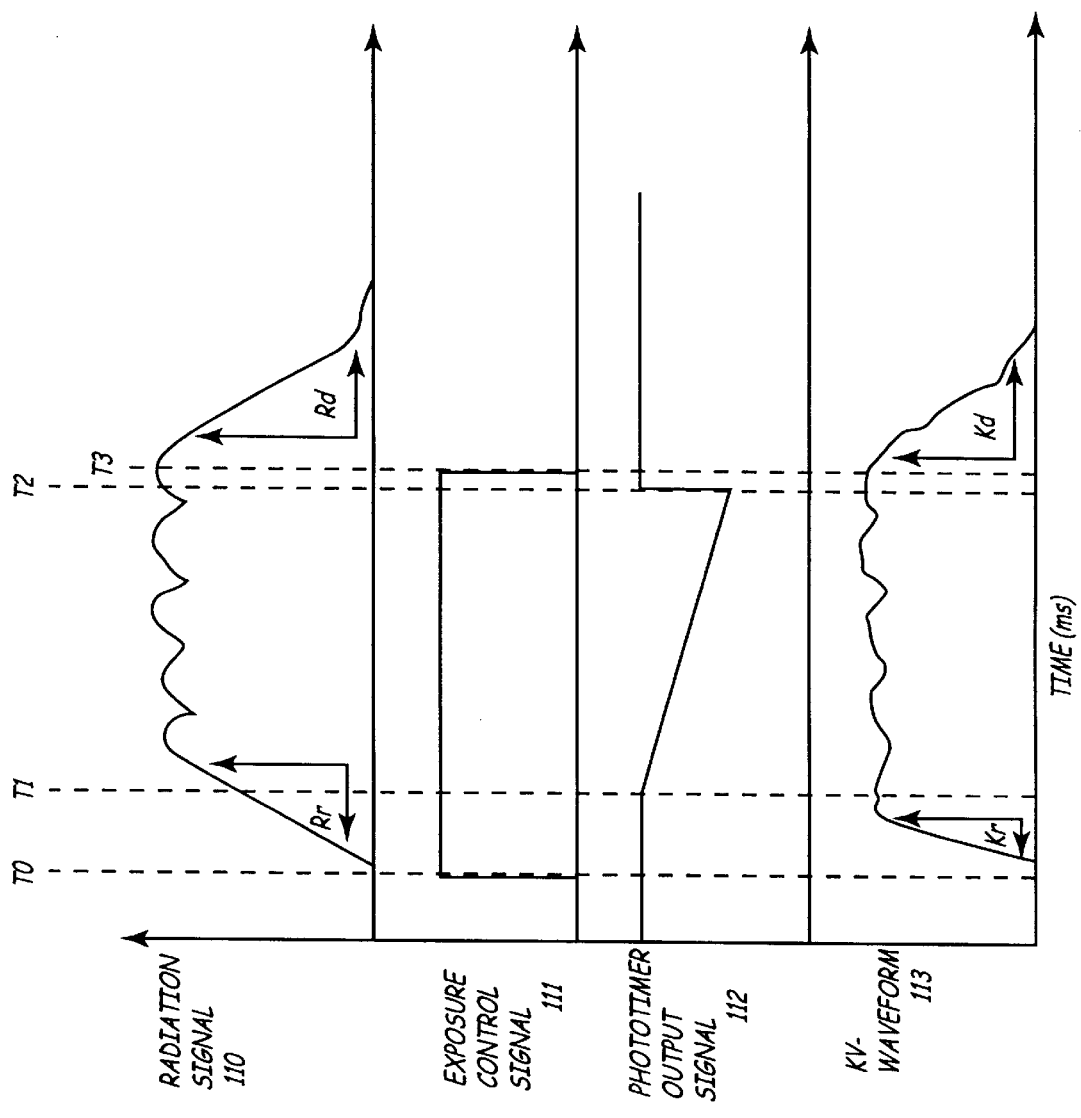
FIG. 10 shows a timing diagram of signals in a typical signal acquisition sequence and processed waveform.

A unique aspect of this invention, not present in the prior art, is the capability for signal and sequence analysis 61 for signals from radiation sensors 5 in Multi-sensor Assembly 1 and External Signal Inputs 6. Consider signals 114, 111, 112, 113 in FIG. 10. Signal 114 is from radiation sensor, 111 is exposure control signal from x-ray generator control fed to external input 6, 112 is a phototimer output signal from Automatic Exposure Control interface to x-ray generator, and 113 is KV-waveform calculated from radiation sensors 5. FIG. 10 represents a typical display of waveforms on the display medium or monitor. The waveforms are presented against time. In order that the system operates according to design specification several sequence and shape criteria of waveforms must be met in real time sequence of events. For example, at time $\tau_0$ so exposure starts as seen from signal 111; at time $\tau_1$ signal 112 ramp is above threshold and builds up until it reaches a predetermined level at time $\tau_2$; However, radiation exposure continues for some more time until time $\tau_3$. Thus, the present device enables evaluation of these intervals and shapes of waveforms to verify or service the system. The rise time Rr, fall time $R_d$ of the radiation waveform, $K_r$ and $K_d$ from calculated kV-waveform is also presented. Several system problems can be assessed, by viewing the waveforms in time sequence, and ability to determine intervals and shapes for system diagnosis.

Figure 11:
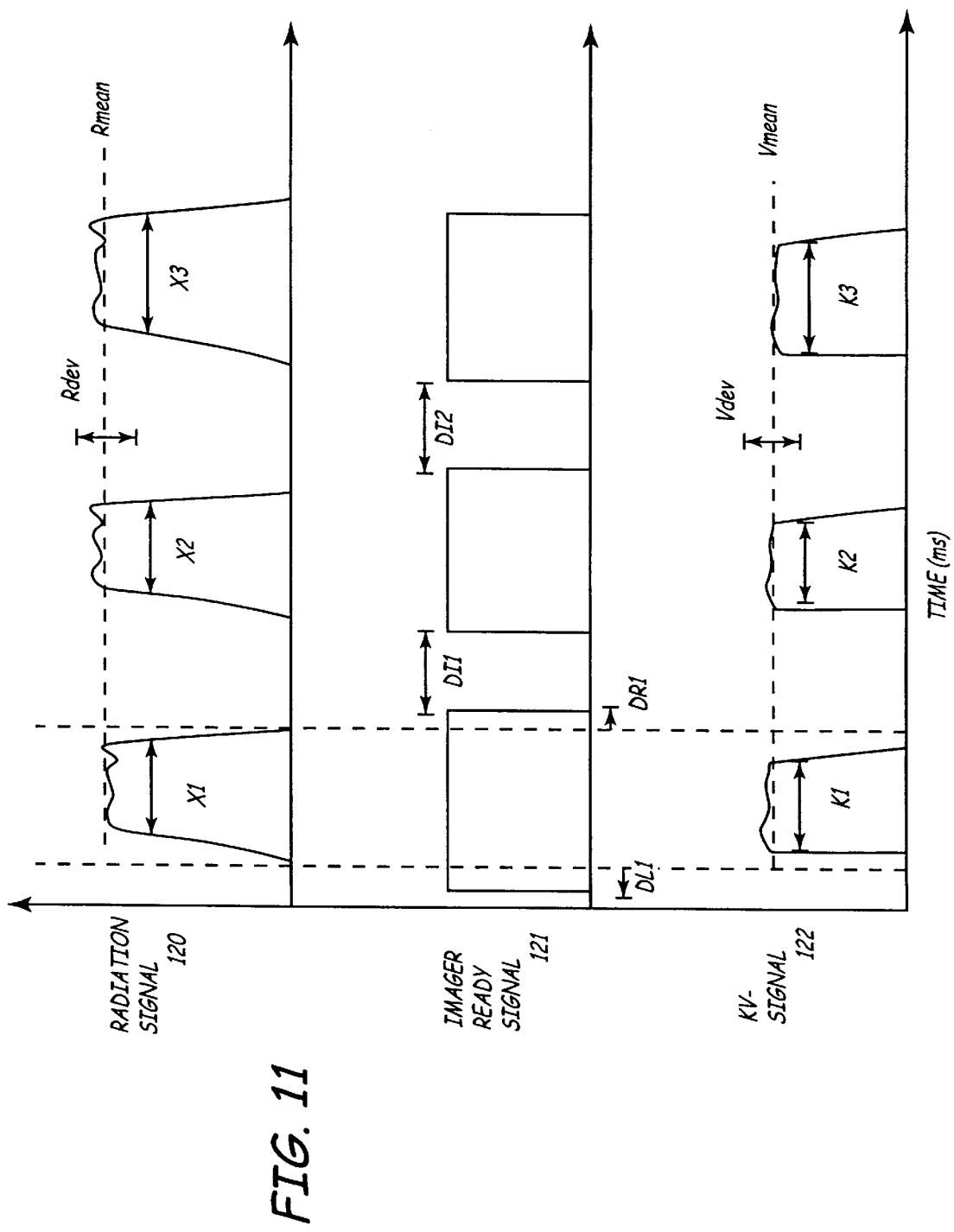
FIG. 11 shows a timing diagram of signals in a typical real time acquisition scan for pulsed film or digital camera imaging using radiation and x-ray generator control/interface.

FIG. 11 illustrates another real time acquisition scan example for multi-image radiation exposure such as used in angiography, cine imaging etc. Radiation signal 120 has several exposure pulses X1, X2, X3 etc. In order to achieve reliable images, stability of the radiation signal mean amplitude, Rmean, and deviation, Rdev, for all pulses is important. In KV signal 122, with corresponding pulses K1, K2, K3 etc., the similar signal parameters are Vmean and Vdev. It is useful to verify or service that the imager (film camera, digital camera etc.) ready signal 121 length is wider than exposure pulse and the intervals DL1, DR1, DI1 are sufficient according to specifications. DL1 assures x-ray exposure starts after imager is ready and DR1 waits until exposure pulse is completed. The inter-pulse intervals DI1, DI2 etc. guarantee that images do not overlap. The stability of these intervals is crucial for correct operation of the system. Thus the present invention is capable of evaluating time and performance relationships between interfaces and x-ray source in terms of radiation and electrical signals. This capability is a unique aspect of this invention.

Figure 12:
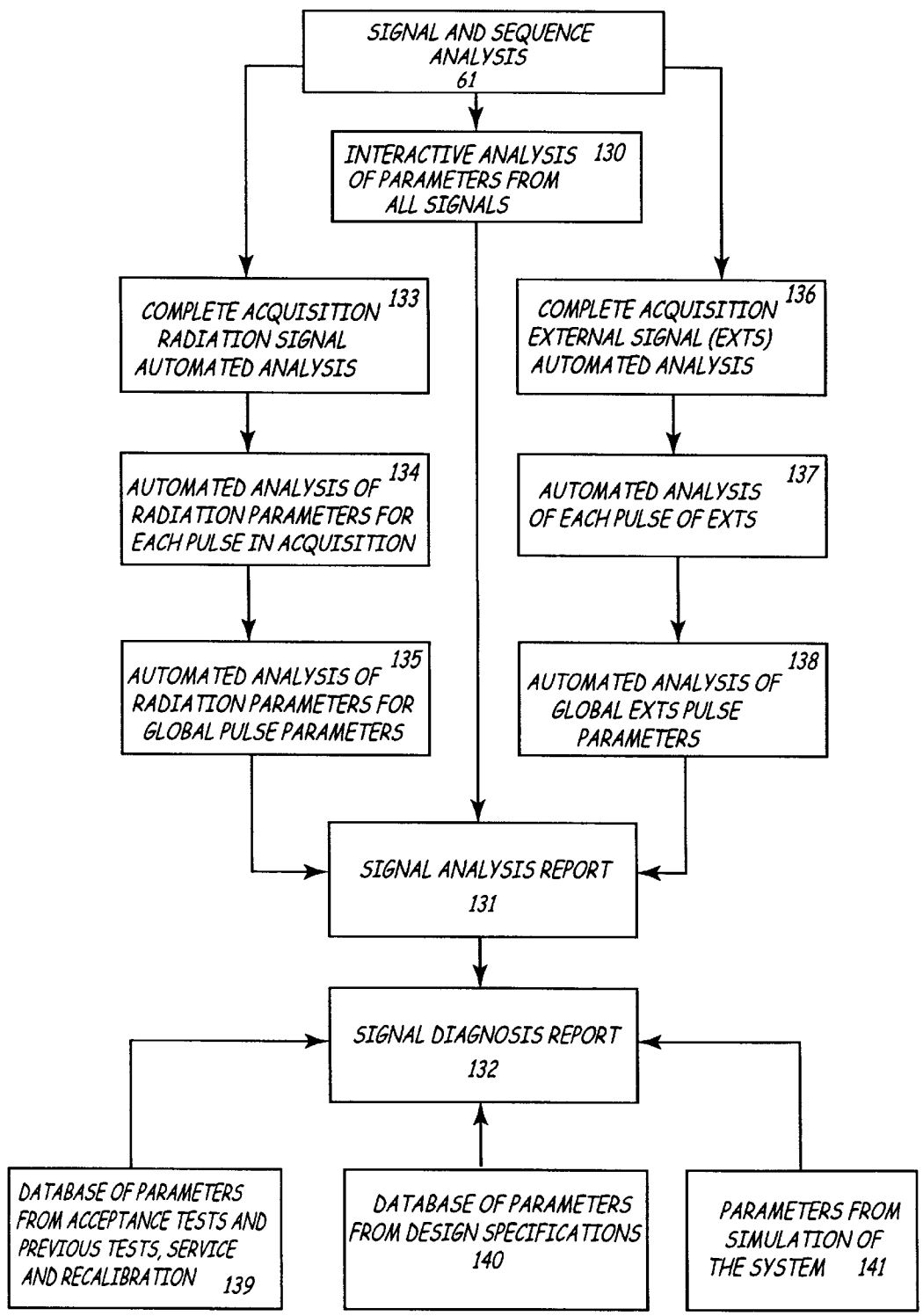
FIG. 12 is a flow chart of a radiation signal and external signal processing procedure.

Signal and sequence analysis 61 includes three processing paths: processing of radiation signals 133, 134, 135 of the Multi-Sensor Assembly, processing of external signals 136, 137, 138, and interactive processing of any signal waveform 130 by the user. Processing procedure 133 is similar to single exposure evaluation method 72 and procedure 134 is similar to single exposure evaluation methods 75, 62, 63, 64, 65, 66 with corrections. Processing of external signals 136 and 137 has been outlined with reference to FIGS. 10 and 11. In procedures 133, 134, 136, 137 multi-pulse processing is accomplished using single exposure processing methods. Procedures 135 and 138 compute global performance parameters for the multi-pulse exposure with reference to stability of values such as means, deviations, intervals from parameters evaluated for each pulse. Based on above analysis, signal performance report 131 and diagnostic report 132 are produced. Diagnostic report 132 deals with problems and solutions. To accomplish this, information from database of Acceptance and previous tests 139 on the same equipment, from database of design specifications 140 and from simulated parameters specific for this system 141. The processing flow is sketched in FIG. 12. The multi-pulse multi-signal processing and producing signal analysis and diagnostic report is a key aspect of this invention.

Figure 13:
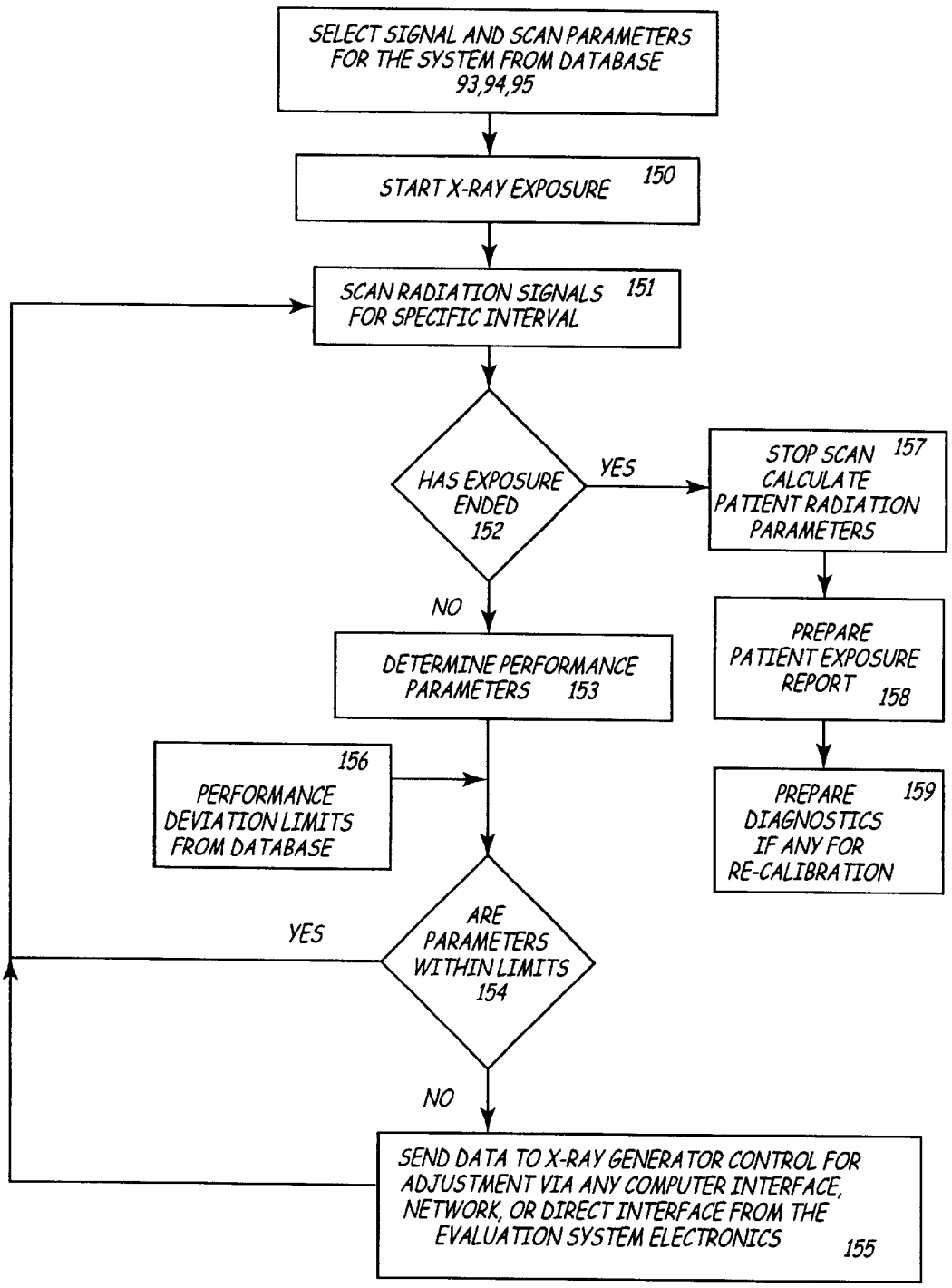
FIG. 13 is a flow chart depicting a procedure for on-line generator control based on radiation performance and preparation of patient exposure and system diagnostics reports.

Using high frequency sampling, a multi sensor assembly, fast data transfer through PC-card and PC-interfaces, a fast computer and software capable of processing data samples as soon as they are acquired, it is possible to control the x-ray generator by feeding the performance parameter information to the generator. This method is outlined in FIG. 13.

As exposure starts 150 radiation signals are scanned 151 or sampled for a short time interval say 3 milliseconds and required parameters are computed 153. On comparing 154 with permissible range 156 of parameters, information is sent to generator via a fast signal interface 155 such as standard computer ports, network or any direct dedicated interface to evaluation system itself. The scan continues until end 152 of exposure and stopped. Calculation of 157 patient technique radiation parameters and Patient Exposure Report 158 can be prepared instantly using measures exposure parameters. In addition, if there was generator problems during the exposure, a diagnostic report 159 is prepared to help re-calibration or service. On line feed back of information to generator on performance during the exposure is a fundamental aspect of this invention.

Figure 14:
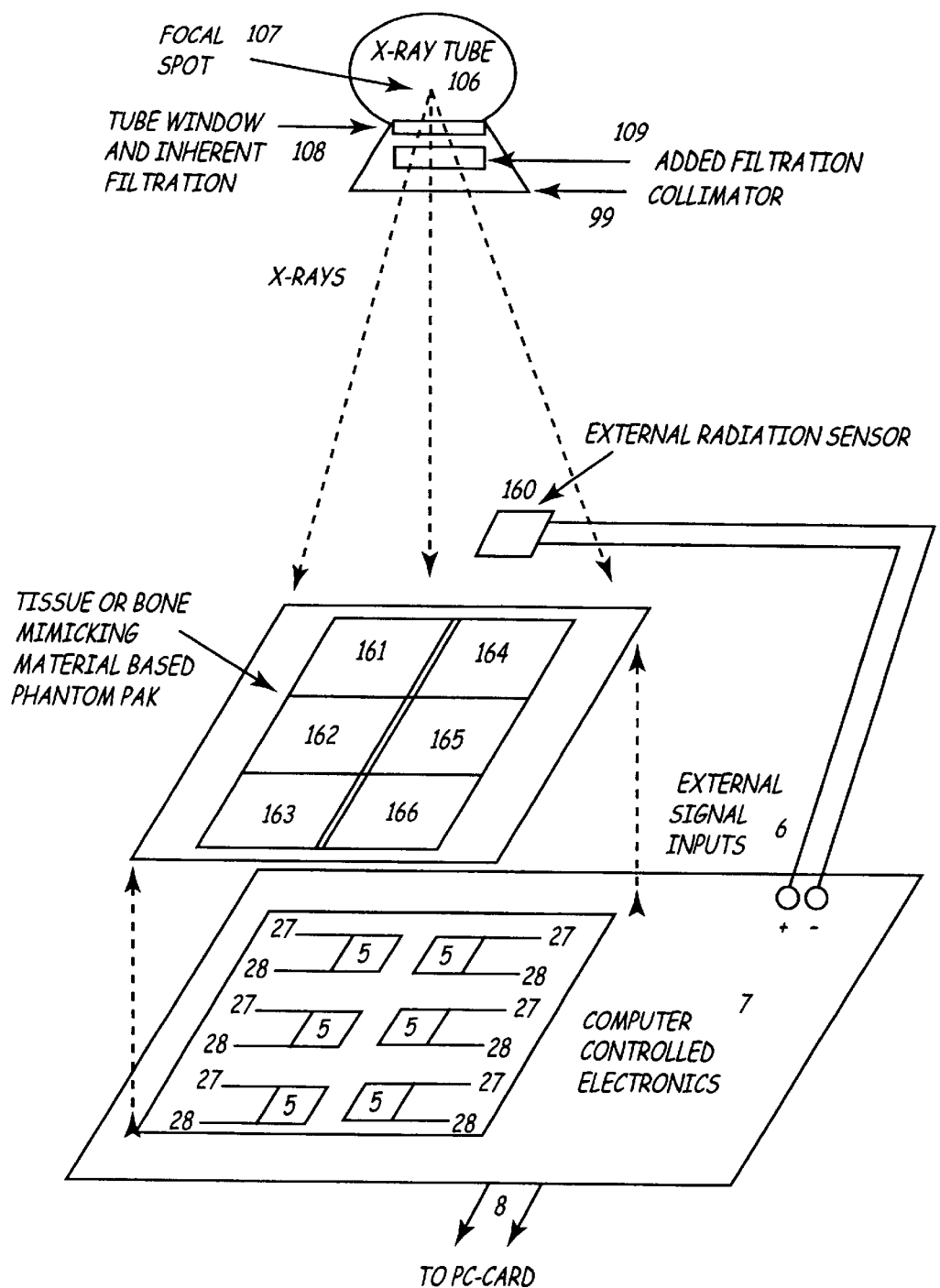
FIG. 14 is a schematic diagram of an apparatus set up for ESE and contrast optimization testing.
Figure 15:
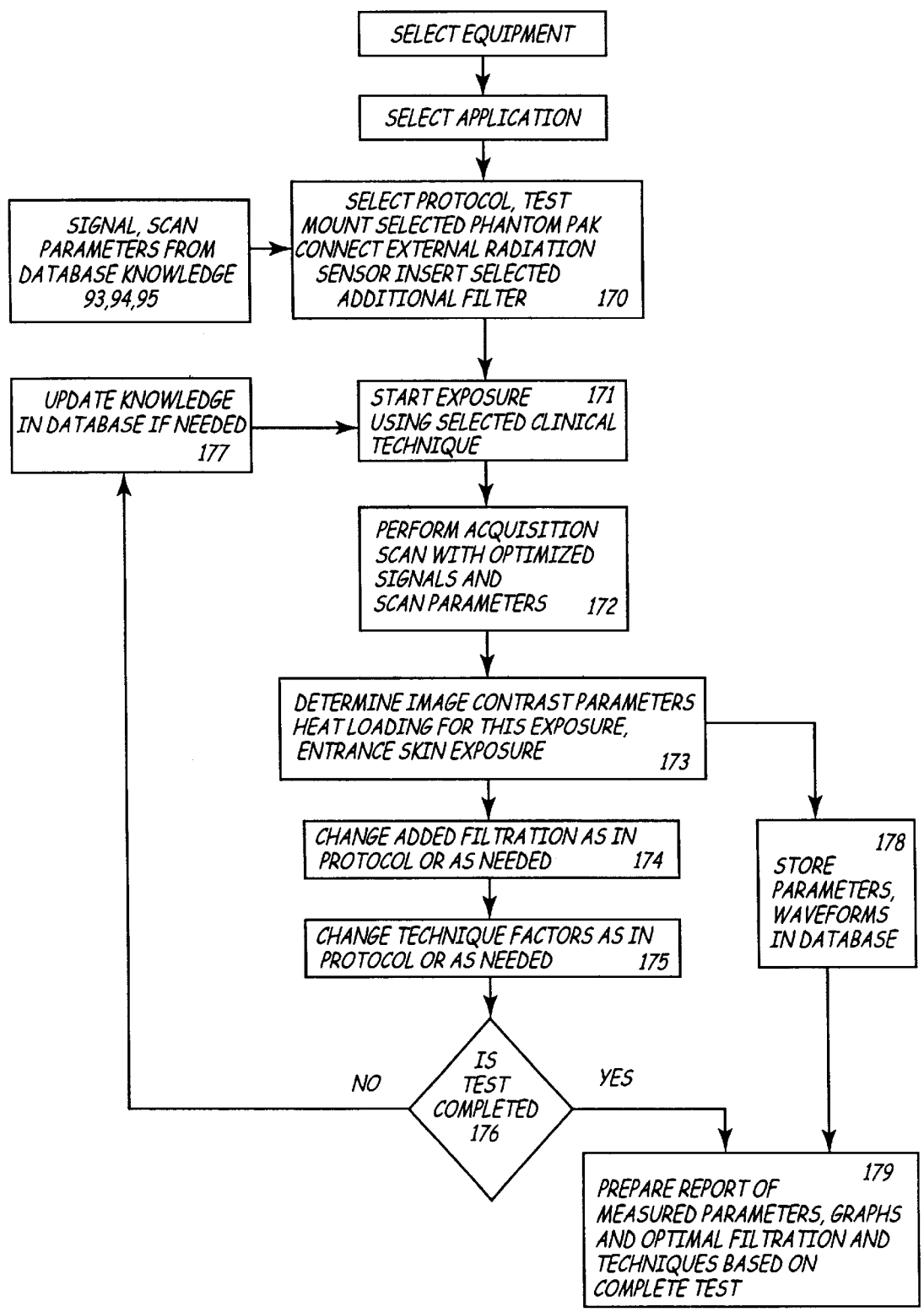
FIG. 15 is a flow chart of an optimization of contrast and ESE testing method.

By using a FilterPak 180 that has tissue or bone mimicking materials for filters in positions 161, 162, 163, 164, 165 and 166, image contrast evaluation can be performed. As illustrated in FIG. 14, the thicknesses of the mimicking material is different at positions. The range of thickness would depend on the application to be evaluated. For example, for mammographic evaluation, the thickness of filters may range from 2 cm to 6 cm of tissue mimicking material or equivalent such as plastic. For abdominal radiographic evaluation, the thickness of filters may range from 15 cm to 25 cm of tissue mimicking material or equivalent such as plastic. Radiation sensors 5 detect x-rays penetrating through different thickness and produce signals corresponding to the transmitted x-rays. The image contrast is a function of ratio of transmitted x-rays depending on thickness. Consider image contrast for a thickness X, given by $\Delta I=(\Delta V/\Delta X)$, where V is the signal produced, $\Delta V$ is change in signal and $\Delta X$ is change in thickness. The function $\Delta I$ is a function of X, technique factor such as kVp, filtration of the system including inherent filtration of x-ray tube window 108 and added filtration 109. The image contrast $\Delta I$ is related to optical density of the film image. When the x-ray response of the sensor assembly is matched to imaging screen in case of film imaging or to image detector in case of electronic imagers, the image contrast evaluation by this method yields results applicable to clinical imaging. Using the apparatus set up in FIG. 14 and procedure given in FIG. 15 using this apparatus, image contrast and entrance skin exposure (ESE) to patient can be optimized. For measurement of ESE, an external radiation sensor 160 is placed above the phantom in the x-ray path and connected to external signal input 6.

Optimization method involves measurement of image contrast and ESE and determining the operating conditions kVp, mAs, and added filtration, for minimum value of tube loading heat units (kVp, mAs product), for maximum image contrast and minimum ESE. This method uses database knowledge 93, 94, 95 and optimal technique. Following steps 171, 172, 173, 174, 175 the necessary data is collected for optimization. Parameters and waveforms are stored in database 178 and report of measured parameters, graphs and optimal conditions are presented. This is a quick and accurate method to optimize the ESE and contrast. This is another important aspect of this invention.

Figure 16:
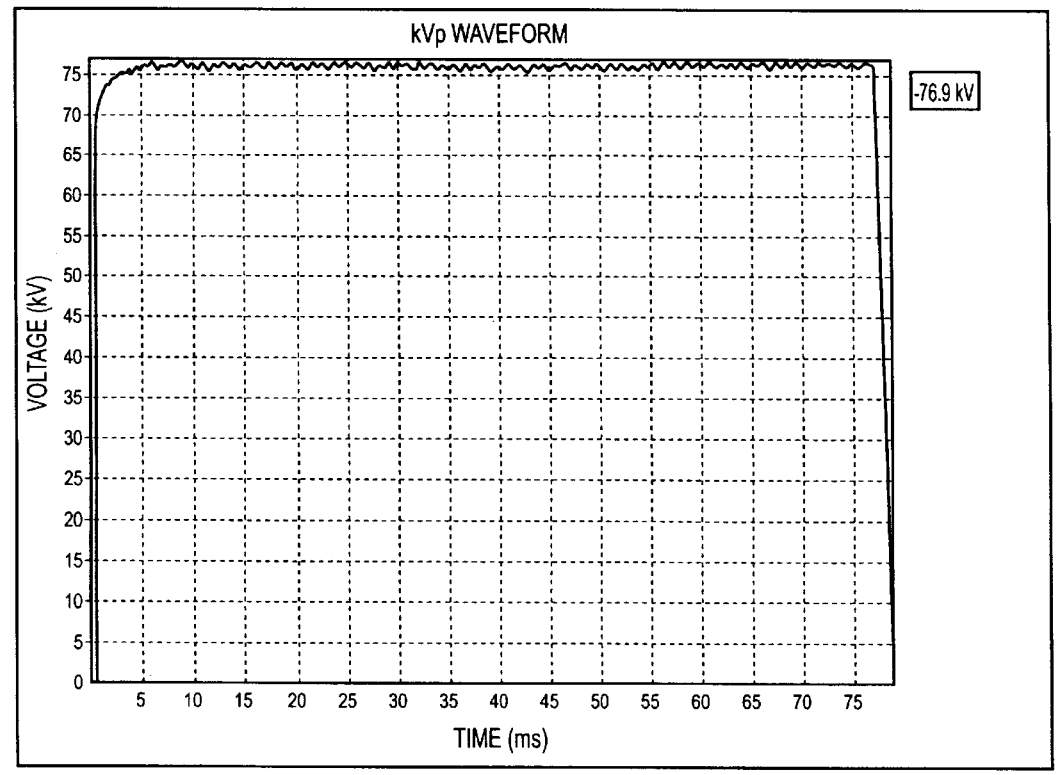
FIG. 16 is a sample of a single exposure report from one embodiment of the present invention.

Generating automatic reports of analysis, diagnosis and potentials based on a single exposure, a single test, or for a summary of all tests is a key aspect of this invention. The report is based on self-consistent evaluation 73 and waveforms 74 that are stored. The report uses knowledge stored of several parameters 74, of simulation 87, design specifications of generator system 89, regulatory compliance information database 85. A typical single exposure report 81 is given in FIG. 16. Test summary report 82 includes parameters that require several exposures such as reproducibility test. Trends report 83 includes values of each parameter from previous tests as stored in database plotted to indicate systematic drift of the parameter. Compliance report presents evaluated parameter values with respect to the PASS/FAIL criteria of a specific regulatory agency. This criteria is available from database 85. Report for a complete test 192 includes all parameters evaluated from all exposures with suitable techniques for that particular test. Based on this information, the system analysis report 86 is produced for the performance of the system as a whole. For example, the reduction in output of the system over a period of time, effects of tube becoming gassy, etc. A diagnostic report 88 is produced to outline problem parameters in the whole application range of that equipment. As an end product of all tests, analysis of results, identification of problems, potential solutions report 90 would be presented using knowledge in database 87 and design parameters 89.

What is claimed is:

1. A system for evaluating a radiation generator having a means for generating radiation and a primary detector means for detecting the generated radiation during normal operation of the radiation generator, the evaluation system comprising:

a second multiple sensor assembly, separate and distinct from the primary detector means, having a plurality of radiation sensors arranged to receive a radiation signal from the radiation generator, each radiation sensor having a sensor output for providing a radiation sensor signal;

a filter assembly having a filter panel for each of the radiation sensors with each filter panel having an associated radiation sensor and being operably interposed between the radiation generator and associated radiation sensor; and a processor assembly operably connected to the multiple sensor assembly to communicate with the multiple sensor assembly, wherein the processor assembly receives the radiation sensor signals for evaluating the performance of the radiation generator; and the processor assembly further comprises a storage device for storing radiation sensor signals.

2. The system of claim 1, wherein the multiple sensor assembly is capable of inputting a plurality of external signal inputs.

3. The system of claim 1, wherein the processor assembly includes a data acquisition and control interface (PC-card) consisting of a Signal Multiplexer, Programmable Gain Amplifier, Analog to Digital Converter, digital input and output control signals and a buffer.

4. The system of claim 1, wherein the processor assembly further comprises software means for using information stored in the processor assembly, for using information available from data obtained from currently acquired signals, and for updating stored information after each data inquisition.

5. The system of claim 1, wherein the multiple sensor assembly includes a signal conditioning circuit for each radiation sensor, wherein the signal conditioning circuit includes:

a) biasing sensors in photo-conductive mode of operation;

b) a load multiplexer;

c) load resistors; and d) digital to analog converter (DAC).

6. The system of claim 5, wherein a load resistor is selected to change the output amplitude of sensor signals, so that suitable digital control signals are sent to the load multiplexer.

7. The system of claim 5, wherein the output of the DAC feeding input to a Programmable Gain Amplifier (PGIA) can be changed by the act of sending suitable digital control signals to the DAC to minimize the offset signal to PGIA.

8. The system of claim 1, wherein the processor assembly includes software means for controlling the digital control signals sent to a DAC.

9. The system of claim 1, wherein the processor assembly includes software means for setting the gain of a PGIA.

10. The system of claim 7, wherein the processor assembly includes software means for scanning the signal inputs to the PGIA.

11. The System of claim 1, wherein the processor assembly includes a method of configuring parameters for asynchronous sampling of each x-ray exposure such that the errors due to asynchronous sampling are minimized.

12. The system of claim 11, wherein the parameters for sampling signals include at least three parameters: (a) sampling period (or frequency) for a single signal; (b) time interval between sampling two successive signals; and (c) time interval between two successive samples of the same signal (scan period).

13. The system of claim 11, wherein the parameters for sampling signals are set sufficiently small by software means to permit transient spikes and breakdowns to be detected.

14. The system of claim 11, wherein the parameters for sampling signals are set corresponding to the generator by software means for accurately reproducing radiation waveforms.

15. The system of claim 10, wherein the act of scanning the signals includes a method of optimizing parameters for every type of radiation exposure: single pulse (radiographic) exposure, continuous fluoroscopic exposure, and pulsed radiographic (or fluoroscopic) exposure.

16. The system of claim 1, wherein the processor assembly includes software means for building a database of x-ray radiation generator characteristics acquired over time for the purpose of trend analysis.

17. The system of claim 1, wherein the processor assembly includes software means for predicting x-ray generator failure.

18. The system of claim 1, wherein the system is adapted for use on different types of x-ray generators and the processor assembly includes software means for optimizing the radiation sensor signals for the different types of x-ray generators including:
a) single pulse;
b) high frequency;
c) angiography;
d) continuous fluoroscopy;
e) pulsed fluoroscopy;
f) mammography;
g) computed tomography.

19. The system of claim 1, wherein the radiation generator is an x-ray generator and wherein the processor assembly evaluates the performance of the radiation generator by determining the Half Value Layer (HVL) of the x-ray beam after a single x-ray exposure.

20. The system of claim 1, wherein the processor assembly evaluates kVp and HVL from a single x-ray exposure.

21. The system of claim 1, wherein the processor assembly receives additional non-radiation based signals and evaluates a number of both radiation and non-radiation based characteristics of the radiation generator from a single x-ray exposure.

22. A system for evaluating a radiation generator, comprising:

a multiple sensor assembly having a plurality of radiation sensors arranged to receive a radiation signal from the radiation generator, each radiation sensor having a sensor output for providing a radiation sensor signal and at least two of the radiation sensors having signal conditioning means for optimizing the signal conditioning during operation, the signal conditioning means comprising means for optimizing the signals for each x-ray exposure by generating digitized offset values when no radiation exposure is taking place, the offset values being applied during operating conditions, and means for iteratively updating the gain of amplification means used to process the radiation signals;

a filter assembly having a filter panel for each of the radiation sensors with each filter panel having an associated radiation sensor and being operably interposed between the radiation generator and associated radiation sensor; and a processor assembly operably connected to the multiple sensor assembly to communicate with the multiple sensor assembly and the signal conditioning means, wherein the processor assembly receives the radiation sensor signals for evaluating the performance of the radiation generator.

23. A system for evaluating a radiation generator, comprising:

a multiple sensor assembly having a plurality of radiation sensors arranged to receive a radiation signal from the radiation generator, each radiation sensor having a sensor output for providing a radiation sensor signal;

a filter assembly having a filter panel for each of the radiation sensors with each filter panel having an associated radiation sensor, at least two of the filters being of different thickness, and each being operably interposed between the radiation generator and associated radiation sensor; and a processor assembly operably connected to the multiple sensor assembly to receive the radiation sensor signals from the multiple sensor assembly and to calculate, from measurements taken during a single x-ray exposure, the value of Half Value Layer (HVL) for the x-ray beam in order to evaluate the performance of the radiation generator.

24. A method for measuring the Half Value Layer (HVL) resulting from a single exposure from an x-ray generator comprising:

interposing a plurality of sensors $s_0$–$s_n$, in the path of the x-ray generator;

interposing between the x-ray generator and the plurality of sensors, a plurality of aluminum filters having different thicknesses $t_0$–$t_n$;

energizing the x-ray generator for a continuous exposure;

measuring the remaining energy of the signals from the sensors after the x-ray beam has passed through the varying thicknesses $t_0$–$t_n$ of the aluminum filters;

storing the measured signals as data;

calculating the ratios $r_1$–$r_n$ corresponding to aluminum filter thickness $t_1$–$t_3$ of each of the measured signals to the strength of the signal when the thinnest filter to is used as a reference signal;

using values $t_1$–$t_n$, from the thickness of the filters and ratios $r_1$–$r_n$ from measured data to determine coefficients $_{0-n}$ using a polynomial function, $t(r)=\alpha_0+\alpha_1 f(r)+\alpha_2 f^2(r) \ldots \alpha_n f^n(r)$ where t represents thickness corresponding to the calculated ratio r and f(r) is a function using each of the ratios r as an independent variable; and calculating the Half Value Layer during a single exposure where r=0.5 and HVL is calculated from $t(r_{HVL}=0.5)$.

25. The method of claim 24, wherein the method further comprises integrating the data for the whole exposure from the measurement of the energy of the signals after the x-ray beam has passed through the varying thickness of aluminum filters.

26. The method of claim 24, wherein the thinnest filter $t_0$ is transparent to the x-ray beam.

27. A system for evaluating an x-ray radiation generator, comprising:
   a) a multiple sensor assembly having four or more independent solid state radiation sensors arranged to receive a radiation signal from the radiation generator, each radiation sensor having a sensor output for providing a radiation sensor signal;
   b) a filter assembly having a filter panel for each of the radiation sensors with each filter panel having an associated radiation sensor and being operably interposed between the radiation generator and associated radiation sensor;
   c) a processor assembly operably connected to the multiple sensor assembly to communicate with the multiple sensor assembly, wherein the processor assembly receives the radiation sensor signals for evaluating the performance of the generator; and
   d) a storage device operably connected to the processor assembly to store the radiation sensor signals.

28. A method for measuring the Half Value Layer (HVL) resulting from a single exposure from an x-ray generator, the method comprising:

interposing a plurality of sensors $s_0$-$s_n$ in the path of the x-ray generator;

energizing the x-ray generator for a continuous exposure;

determining a reference signal by measuring the energy of the signal received by sensor $s_0$;

interposing between the x-ray generator and the plurality of sensors, a plurality of aluminum filters having different thickness $t_1$-$t_n$;

measuring the remaining energy of the signals from sensors $s_1$-$s_n$ after the x-ray beam has passed through the varying thicknesses $t_1$-$t_n$ of the aluminum filters;

storing the value of the reference signal from sensor so and the measured values from sensors $s_1$-$s_n$ as data calculating the ratios $r_1$-$r_n$ corresponding to aluminum filter thickness $t_1$-$t_3$ of the strength of each the measured signals from sensors $s_1$-$s_n$ to the strength of the reference signal as measured by sensor $s_0$;

using values $t_1$-$t_n$, from the thickness of the filters and ratios $r_1$-$r_n$ from measured data to determine coefficients $_{0-n}$ using a polynomial function, $t(r)=\alpha_0+\alpha_1 f(r)+\alpha_2 f^2(r) \ldots \alpha_n f^n(r)$ where t represents thickness corresponding to the calculated ratios r and f(r) is a function using each of the ratios r as an independent variable; and calculating the Half Value Layer during the single exposure when r=0.5 and the HVL is calculated from $t(r_{HVL}=0.5)$.

* * * * *

UNITED STATES PATENT AND TRADEMARK OFFICE
CERTIFICATE OF CORRECTION

PATENT NO. : 6,454,460 B1
DATED : September 24, 2002
INVENTOR(S) : Naganathasastrigal Ramanathan and Vijay Ramanathan It is certified that error appears in the above-identified patent and that said Letters Patent is hereby corrected as shown below:

Column 10,
Line 1, "$t(r) = \alpha_0 + \alpha_1 f(r) + \alpha_2 (r)$" should read -- $t(r) = \alpha_0 + \alpha_1 f(r) + \alpha_2 f^2(r)$ --

Column 12,
Line 7, "at time $\tau_0$ so exposure" should read -- at time $\tau_0$ exposure --

Column 18,
Line 13, "signal from sensor so" should read -- signal from sensor $s_0$ --

Signed and Sealed this

Tenth Day of June, 2003

JAMES E. ROGAN
*Director of the United States Patent and Trademark Office*